(12) United States Patent
Seshi

(10) Patent No.: US 7,303,769 B2
(45) Date of Patent: *Dec. 4, 2007

(54) METHOD FOR PURIFYING PLURI-DIFFERENTIATED MESENCHYMAL PROGENITOR CELLS

(75) Inventor: Beerelli Seshi, Tampa, FL (US)

(73) Assignee: University of South Florida, Tampa, FL (US)

( * ) Notice: Subject to any disclaimer, the term of this patent is extended or adjusted under 35 U.S.C. 154(b) by 188 days.

This patent is subject to a terminal disclaimer.

(21) Appl. No.: 11/055,292

(22) Filed: Feb. 10, 2005

(65) Prior Publication Data

US 2005/0142119 A1 Jun. 30, 2005

Related U.S. Application Data

(63) Continuation of application No. 09/914,508, filed as application No. PCT/US01/16408 on May 21, 2001, now Pat. No. 6,936,281.

(60) Provisional application No. 60/277,700, filed on Mar. 21, 2001, provisional application No. 60/209,245, filed on Jun. 5, 2000.

(51) Int. Cl.
*A61K 35/26* (2006.01)
*A61K 35/28* (2006.01)
*C12N 5/00* (2006.01)
*C12N 5/02* (2006.01)

(52) U.S. Cl. ............. 424/577; 424/937; 424/537; 435/372; 435/383

(58) Field of Classification Search ............. None
See application file for complete search history.

(56) References Cited

U.S. PATENT DOCUMENTS

| | | |
|---|---|---|
| 5,226,914 A | 7/1993 | Caplan et al. |
| 5,486,359 A | 1/1996 | Caplan et al. |
| 5,521,067 A | 5/1996 | Seshi |
| 5,733,542 A | 3/1998 | Haynesworth et al. |
| 5,811,094 A | 9/1998 | Caplan et al. |
| 5,879,940 A | 3/1999 | Torok-Storb et al. |
| 5,942,225 A | 8/1999 | Bruder et al. |
| 6,010,696 A | 1/2000 | Caplan et al. |
| 6,149,902 A | 11/2000 | Artavanis-Tsakonas et al. |
| 2003/0203483 A1* | 10/2003 | Seshi ............ 435/366 |
| 2005/0059147 A1* | 3/2005 | Seshi ............ 435/366 |

FOREIGN PATENT DOCUMENTS

WO WO 01/94541 A2 12/2001
WO WO 03/029432 A2 4/2003

OTHER PUBLICATIONS

Chakrabarti, O. and S. Krishna "Molecular interactions of 'high risk' human papillomaviruses E6 and E7 oncoproteins: implications for tumour progession" *J. Biosci.*, 2003, 28(3):337-348.

Charbord, P. et al. "Stromal cells from human long-term marrow cultures, but not cultured marrow fibroblasts, phagocytose horse serum constituents: studies with a monoclonal antibody that reacts with a species-specific epitope common to multiple horse serum proteins" *Exp. Hematol.*, 1987, 15:72-77.

Conget, P.A. and J.J. Minguell "Phenotypical and functional properties of human bone marrow mesenchymal progenitor cells" *J. Cell. Physiol.*, Oct. 1999, 181:67-73.

Dennis, J.E. et al. "A quadripotential mesenchymal progenitor cell isolated from the marrow of an adult mouse" *J. Bone and Mineral Res.*, 1999, 14(5):700-709.

Deunsing, S. and K. Munger "The human papillomavirus type 16 E6 and E7 oncoproteins independently induce numerical and structural chromosome instability" *Cancer Res.*, 2002, 62:7075-7082.

Deunsing, S. et al. "The human papillomavirus type 16 E6 and E7 oncoproteins cooperate to induce mitotic defects and genomic instability by uncoupling centrosome duplication from the cell division cycle" *PNAS*, 2000, 97(18):10002-10007.

Dorshkind, K. "Multilineage development from adult bone marrow cells" *Nature Immunology*, 2002, 3(4):311-313.

Durst, M. et al. "Inverse relationship between human papilomavirus (HPV) type 16 early gene expression and cell differentiation in nude mouse epithelial cysts and tumors induced by HPV-positive human cell lines" *J. Virology*, 1991, 65(2):796-804.

Friedenstein, A.J. et al. "Fibroblast precursors in normal and irradiated mouse hematopoietic organs" *Exp. Hemat.*, 1976, 4:267-274.

Eaves, A.C. and C.J. Eaves "Maintenance and proliferation control of primitive hemopoietic progenitors in long-term cultures of human marrow cells" *Blood Cells*, 1988, 14:355-368.

Gerson; S.L. "Mesenchymal stem cells: No longer second class marrow citizens" *Nature Med.*, 1999, 5(3):262-264.

Graf, L. et al. "Gene expression profiling of the functionally distinct human bone marrow stromal cell lines HS-5 and HS-27a" *Blood*, 2002, 100(4):1509-1511.

Gravitt, P. "HPV: The ultimate cancer initiator?" *HPV Today*, No. 3, Sep. 2003, pp. 1-4.

Haynesworth, S.E. et al. "Characterization of cells with osteogenic potential from human marrow" *Bone*, 1992, 13:81-88.

Haynesworth, S.E. et al. "Cell surface antigens on human marrow-derived mesenchymal cells are detected by monoclonal antibodies" *Bone*, 1992, 13:69-80.

Henderson, A.J. et al. "Functional characterization of two stromal cell lines that support B lymphopoiesis" *J Immunology*, 1990, 145:423-428.

Hicok, K.C. et al. "Development and characterization of conditionally immortalized osteoblast precursor cell lines from human bone marrow stroma" *J. Bone and Mineral Res.*, 1998, 13(2):205-217.

(Continued)

*Primary Examiner*—Michail Belyavskyi
(74) *Attorney, Agent, or Firm*—Saliwanchik, Lloyd & Saliwanchik

(57) ABSTRACT

There is provided an isolated pluri-differentiated human mesenchymal progenitor cells (MPCs), a method for isolating and purifying human mesenchymal progenitor cells from Dexter-type cultures, and characterization of and uses, particularly therapeutic uses for such cells. Specifically, there is provided isolated MPCs which can be used for diagnostic purposes, to enhance the engraftment of hematopoietic progenitor cells, enhance bone marrow transplantation, or aid in the treatment or prevention of graft versus host disease.

9 Claims, 12 Drawing Sheets

OTHER PUBLICATIONS

Horwitz, E.M. et al. "Transplantability and therapeutic effects of bone marrow-derived mesenchymal cells in children with osteogenesis imperfecta" *Nature Med.*, 1999, 5(3):309-313.

Iwata, M. et al. "Functional interleukin-7 receptors (IL7R) are expressed by marrow stromal cells: binding of IL-7 increases levels of IL-6 mRNA and secreted protein" Aug. 2002 (epub date May 2002), 100:1318-1325.

Keating, A. et al. "Donor origin of the in vitro haematopoietic microenvironment after marrow transplantation in man" *Nature*, 1982, 298:280-283.

Kelly, K.A. and J.M. Gimble "1,25-Dihydroxy vitamin $D_3$ inhibits adipocyte differentiation and gene expression in murine bone marrow stromal cell clones and primary cultures" *Endocrinology*, 1998, 139:2622-2628.

Koc, O.N. et al. "Bone marrow-derived mesenchymal stem cells remain host-derived despite successful hematopoietic engraftment after allogeneic transplantation in patients with lysosomal and peroxisomal storage diseases" *Exp. Hematology*, 1999, 27:1675-1681.

Kopen, G.C. et al. "Marrow stromal cells migrate throughout forebrain and cerebellum, and they differentiate into astrocytes after injection into neonatal mouse brains" *Proc. Natl. Acad. Sci. USA*, 1999, 96:10711-10716.

Liesveld, J.L. et al. "Characterization of human marrow stromal cells: Role in progenitor cell binding and granulopoiesi" *Blood*, 1989, 73(7):1794-1800.

Moore, M.A.S. et al. "Prolonged hematopoiesis in a primate bone marrow culture system: Characteristics of stem cell production and the hematopoietic microenvironment" *Blood*, 1979, 54(4):775-793.

Park, S.R. et al. "Interconversion potential of cloned human marrow adipocytes in vitro" *Bone*, 1999, 24(6):549-554.

Penn, P.E. et al. "Dissecting the hematopoietic microenvironment. IX. Further characterization of murine bone marrow stromal cells" *Blood*, 1993, 81(5):1205-1213.

Pessina, A. et al. "Expression of B cell markers on SR-4987 cells derived from murine bone marrow stroma" *Exp. Hematology*, 1997, 25:536-541.

Prockop, D.J. "Marrow stromal cells as stem cells for nonhematopoietic tissues" *Science*, 1997, 276:71-74.

Roecklein, B.A. and B. Torok-Storb "Functionally distinct human marrow stromal cell lines immortalized by transduction with the human papilloma virus E6/E7 genes" *Blood*, 1995, 85(4):997-1005.

Seshi, B. et al. "Multilineage gene expression in human bone marrow stromal cells as evidenced by single-cell microarray analysis" *Blood Cells, Molecules, and Diseases*, 2003, 31:268-285.

Siler, U. et al. "Laminin γ2 chain as a stromal cell marker of the human bone marrow microenvironment" *Brit. J. Haematology*, 2002, 119:212-220.

Simmons, P.J. et al. "Host origin of marrow stromal cells following allogeneic bone marrow transplantation" *Nature*, 1987, 328:429-432.

Singer, J.W. et al. "Evidence for a stem cell common to hematopoiesis and its in vitro microenvironment: Studies of patients with clonal hematopoietic neoplasia" *Leukemia Res.*, 1985, 8(4):535-545.

Stedman, T.L., Stedman's Medical Dictionary, 5th Edition, 1984, pp. 931-932.

Stoppler, H. et al. "The human papillomavirus type 16 E6 and E7 oncoproteins dissociate cellular telomerase activity from the maintenance of telomere length" *J. Biol. Chem.*, 1997, 272(20):13332-13337.

Taichman, R.S. et al. "Human osteoblasts support human hematopoietic progenitor cells in in vitro bone marrow cultures" *Blood*, 1996, 87(2):518-524.

Torok-Storb, B., ATCC Catalog, ATCC No. CRL-2496.

Torok-Storb, B. et al. "Dissecting the marrow microenvironment" *Ann. NY Acad. Sci.*, 1999, 872:164-170.

Taichman, R.S. and S.G. Emerson "Human osteoblasts support hematopoiesis through the production of granulocyte colony-stimulating factor" *J. Exp. Med.*, 1994, 179:1677-1682.

Terada, N. et al. "Bone marrow cells adopt the phenotype of other cells by spontaneous cell fusion" *Nature*, 2002, 416:542-545.

Thomas, T. et al. "Leptin acts on human marrow stromal cells to enhance differentiation to osteoblasts and to inhibit differentiation to adipocytes" *Endocrinology*, 1999, 140:1630-1638.

Tremain, N. et al. "MicroSAGE analysis of 2,353 expressed genes in a single cell-derived colony of undifferentiated human mesenchymal stem cells reveals mRNAs of multiple cell lineages" *Stem Cells*, 2001, 19:408-418.

Wineman, J. et al. "Functional heterogeneity of the hematopoietic microenvironment: Rare stromal elements maintain long-term repopulating stem cells" *Blood*, 1996, 87(10):4082-4090.

Woodbury, D. et al. "Adult bone marrow stromal stem cells express germline, ectodermal, endodermal, and mesodermal genes prior to neurogenesis" *J. Neuroscience Res.*, 2002, 96:908-917.

Yamazaki, K. et al. "A comparative morphometric study on the ultrastructure of adherent cells in long-term bone marrow culture from normal and cogenitally anemic mice" *Blood Cells*, 1989, 15:343-364.

Dexter, T.M. et al. "conditions Controlling the Proliferation of Haemopoietic Stem Cells In Vitro" *J. Cell. Physiol.*, 1977, 91(3):335-344.

Greenberger, J.S. "Sensitivity of corticosteroid-dependent insulin-resistant lipogenesis in marrow preadipocytes of obese-diabetic (db/db) mice" *Nature*, Oct. 26, 1978, 275:752-754.

Seshi, B. et al. "Human Bone Marrow Stromal Cell: Coexpression of Markers Specific for Multiple Mesenchymal Cell Lineages" *Blood Cells, Molecules, and Diseases*, Jun. 2000, 26(3):234-246.

Seshi, B. "Discovery of Novel Hematopoietic Cell.Adhesion Molecules From Human Bone Marrow Stromal Cell Membrane Protein Extracts by a New Cell-Blotting Technique" *Blood*, May 1994, 83(9):2399-2409.

Bordignon, C. et al. "Cell Therapy: Achievements and Perspectives" *Haematologica*, 1999, 84:1110-1149.

Gartner, S. and H.S. Kaplan "Long-term culture of human bone marrow cells" *Proc. Natl. Acad. Sci. USA*, Aug. 1980, 77(8):4756-4759.

Dexter, T.M. et al. "Long-Term Marrow Culture: An Overview of Techniques and Experience" in Long-Term Bone Marrow Culture, Wright, D.G. et al., Eds., 1984, pp. 57-96.

Marini, F. et al. "Mesenchymal Stem Cells (MSC) from Patients with Chronic Myelogenous Leukemia (CML) Patients can be Transduced with Common Gene Transfer Vectors at High Efficiency, and are Genotypically Normal" Abstract from American Society of Hematology 42nd Annual Meeting, Part 1. Dec. 1-5, 2000. San Francisco, Ca.

Keating, A. et al. "Effect of Different Promoters on Expression of Genes Introduced into Hematopoietic and Marrow Stromal Cells by Electroporation" *Exp. Hematol.*, 1990, 18:99-102.

Lazarus, H.M. et al. "Human bone marrow-derived mesenchymal (stromal) progenitor cells (MPCs) cannot be recovered from peripheral blood progenitor cell collections" *J. Hemotatherapy*, 1997, 6:447-455.

Simmons, P.J. et al. "Isolation, characterization and functional activity of human marrow stromal progenitors in hemopoiesis" *Advances in Bone Marrow Purging and Processing*, 1994, 389:271-280.

Sullivan, A.K. et al. "Cellular composition of rat bone marrow stroma" *Lab. Invest.*, 1989, 60(4):667-676.

Seshi, B. "Proteomics knocks on hematology's door" *Blood*, May 2004, 103(10):3607.

Pittenger et al. *Science*, 1999, 284:143-147.

Ager et al. *Immune Receptor Supplement. Immunology Today*, 1997, pp. 1-35.

Bordignon et al. *Haematologica*, 1999, 84:1110-1149.

Majumdar et al. "Phenotypic and functional comparison of cultures of marrow-derived mesenchymal cells (MSCs) and stromal cells" *J. Cell. Physiol.*, 1998, 176:57-66.

Dictionary of Cell Biology, ed. Lackie et al., 1989, Academic Press, Harcourt Brace Jovanovich, p. 189.

Minguell, J.J. et al. "Nonstimulated human uncommitted mesenchymal stem cells express cell markers of mesenchymal and neural lineages" *Stem Cells and Develop.*, 2005, 14:408-414.

Seshi, B. "An integrated approach to mapping the proteome of the human bone marrow stromal cell" *Proteomics*, 2006, 6:5169-5182.

McCune, J.M. et al. "The SCID-hu mouse: murine model for the analysis of human hematolymphoid differentiation and function" *Science*, 1988, 241:1632-1639.

Yamaguchi, Y. et al. "Detection of mutations of *p*53 tumor suppressor gene in pancreatic juice and its application to diagnosis of patients with pancreatic cancer: Comparison with K-*ras* mutation" *Clin. Canc. Res.*, 1999, 5:1147-1153.

\* cited by examiner

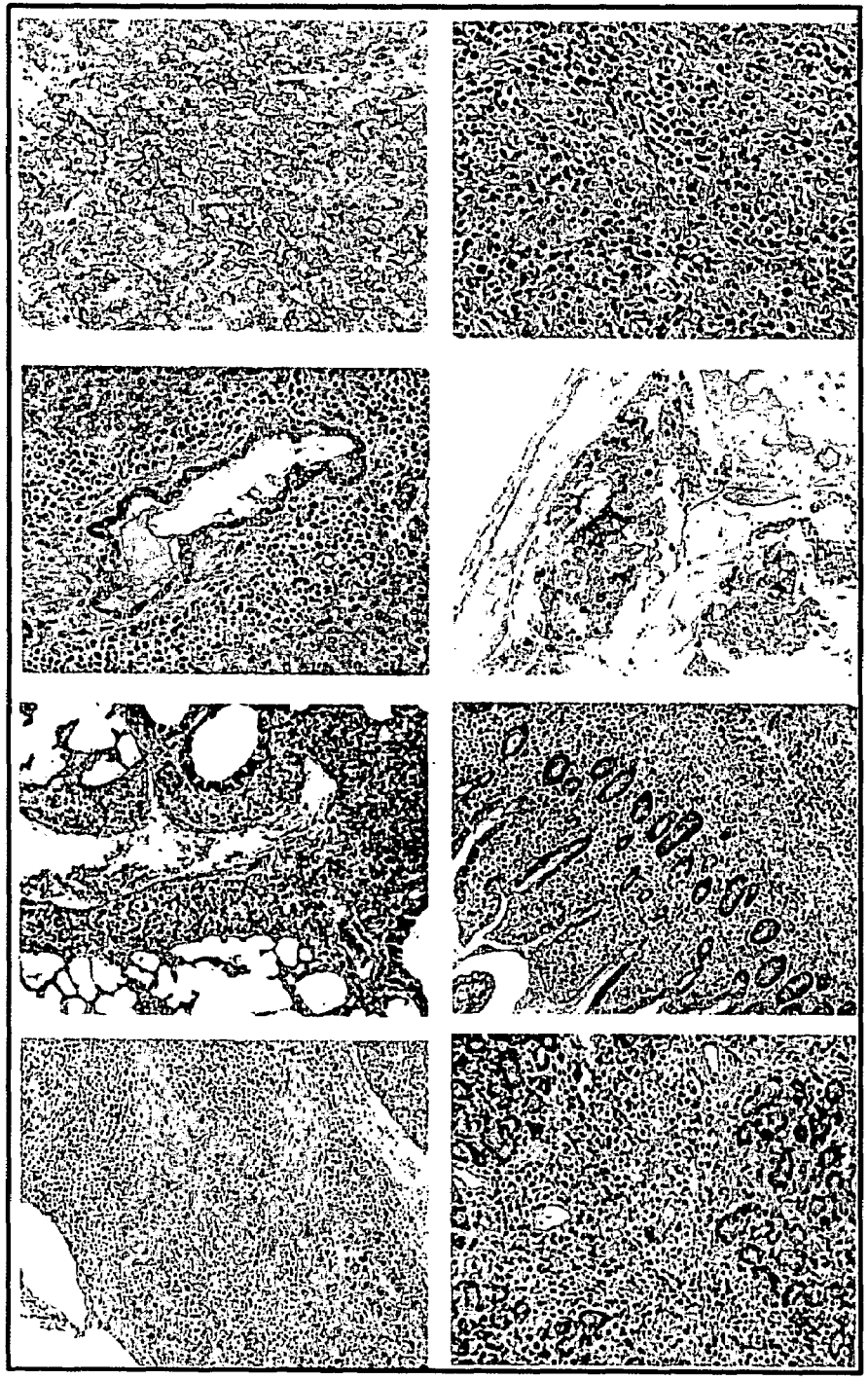

METHOD FOR PURIFYING PLURI-DIFFERENTIATED MESENCHYMAL PROGENITOR CELLS

CROSS-REFERENCE TO RELATED APPLICATIONS

The present application is a continuation of U.S. application Ser. No. 09/914,508, filed Nov. 7, 2001, now U.S. Pat. No. 6,936,281, issued Aug. 30, 2005, which is the National Stage of International Application Number PCT/US10/16408, filed May 21, 2001, which claims benefit of U.S. Provisional Application Ser. Nos. 60/277,700, filed Mar. 21, 2001, and 60/209,245, filed Jun. 5, 2000, each of which is hereby incorporated by reference herein in its entirety, including any figures, tables, nucleic acid sequences, amino acid sequences, and drawings.

GOVERNMENT SUPPORT

The subject matter of this application has been supported by a research grant from the National Institutes of Health under grant No. R29 HL 59683. Accordingly, the government has certain rights in this invention.

FIELD OF THE INVENTION

The present invention relates to pluri-differentiated mesenchymal progenitor cells that are isolated from hematopoietic cells and macrophages in Dexter-type cultures and therapeutic uses for such cells. More specifically, the isolated mesenchymal progenitor cells can be used for diagnostic purposes, to enhance engraftment of human bone marrow or hematopoietic progenitor cells, or to treat graft versus host disease.

BACKGROUND OF THE INVENTION

Bone marrow, the site of blood cell production and home to various leukemia and lymphoma cells, comprises a complex cellular population including hematopoietic progenitor or stem cells and the stromal cells that support them. Hematopoietic stem cells have the capacity for self-regeneration and for generating all blood cell lineages while stromal stem cells have the capacity for self-renewal and for producing the hematopoietic microenvironment.

Two bone-marrow culture systems introduced in the mid-1970's have evolved as favored media for the in vitro analysis of mesengenesis and hematopoiesis. The Friedenstein culture system was introduced in 1976 as a media for the analysis and study of mesengenesis (Friedenstein et al. *Exp Hematol*, 1976, 4:267-274). In order to obtain mesenchymal stem cells (MSCs) for expansion in the culture medium, it is necessary to first isolate rare pluripotant mesenchymal stem cells from other cells in the bone marrow. In the Friedenstein culture system, isolating the non-hematopoietic cells is achieved by utilizing their tendency to adhere to plastic. Once isolated, a monolayer of homogeneous, undifferentiated stromal cells is then grown in the culture medium, in the absence of hematopoietic cells. The stromal cells from this system have the potential to differentiate into discrete mesenchymal tissues, namely bone, cartilage, adipose tissue and muscle depending on specific growth supplements. These MSCs have been the target of extensive investigation including exploration of their potential clinical utility in repair or replacement of genetically damaged mesenchymal tissues.

In 1977, Dexter et al. developed another bone marrow culture system for the study of hematopoiesis (Dexter et al. *J Cell Physiol*, 1977, 91:335-344). The Dexter culture does not require isolation of the mesenchymal cells before culturing, thus the monolayer of stromal cells is grown in the presence of hematopoietic cells. Greenberger later modified the Dexter system by the addition of hydrocortisone to the culture medium, making it more reproducible (Greenberger, *Nature*, 1978, 275:752-754).

Based on the Dexter system's ability to support sustained growth and preservation of hematopoietic progenitor cells, it has become the standard in vitro model for the study of hematopoiesis. Although the Dexter-type stromal cells and the MSCs in Friedenstein-type cultures express similar cytokine/growth factor profiles, the Dexter cultures have been found to be more efficient at maintaining preservation of hematopoietic progenitor cells. Over the last 23 years, questions have remained as to whether the cells from the Dexter cultures retained the potential to differentiate, like the MSCs in the Friedenstein culture, or whether they have differentiated into another and discrete phenotype due to their interaction with the hematopoietic cells (Prockop, *Science*, April 1997, 276(5309):71-74). It has been widely believed that the stromal cells of the Dexter cultures are a heterogeneous mixture of adipocytes, osteoblasts, fibroblasts, muscle cells, and vascular endothelial cells.

The in vitro analysis and study of hematopoiesis in Friedenstein and Dexter culture systems has been of great importance in both veterinary and human medicine. A number of diseases and immune disorders, as well as malignancies, appear to be related to disruptions within the hematopoietic system.

Allogeneic bone marrow transplantation is the preferred treatment for a variety of malignant and genetic diseases of the blood and blood-forming cells. The success rate of allogeneic bone marrow transplantation is, in large part, dependent on the ability to closely match the major histocompatibility complex of the donor cells with that of the recipient cells to minimize the antigenic differences between the donor and the recipient, thereby reducing the frequency of host-versus-graft responses and graft-versus-host disease (GvHD). Unfortunately, only about 20% of all potential candidates for bone marrow transplantation have a suitable family member match.

Bone marrow transplantation can be offered to those patients who lack an appropriate sibling donor by using bone marrow from antigenically matched, genetically unrelated donors (identified through a national registry), or by using bone marrow from a genetically related sibling or parent whose transplantation antigens differ by one to three of six human leukocyte antigens from those of the patient. Unfortunately, the likelihood of fatal GvHD and/or graft rejection increases from 20% for matched sibling donors to 50% in the cases of matched, unrelated donors and un-matched donors from the patient's family.

The potential benefits of bone marrow transplantation have stimulated research on the cause and prevention of GvHD. The removal of T cells from the bone marrow obtained from matched unrelated or unmatched sibling donors results in a decreased incidence of graft versus host reactions, but an increased incidence of rejection of the allogeneic bone marrow graft by the patient.

Current therapy for GvHD is imperfect, and the disease can be disfiguring and/or lethal. Thus, risk of GvHD restricts the use of bone marrow transplantation to patients with otherwise fatal diseases, such as severe immunodeficiency disorders, severe aplastic anemia, and malignancies.

The potential to enhance engraftment of bone marrow or stem cells from antigenically mismatched donors to patients without graft rejection or GvHD would greatly extend the availability of bone marrow transplantation to those patients without an antigenically matched sibling donor.

Thus, it would be useful to develop methods of improving bone marrow transplantation by enhancing the engraftment of bone marrow or hematopoietic progenitor cells and/or decreasing the occurrence of graft rejection or GvHD in allogenic transplants.

Studies of hematopoiesis and mesengenesis and the urgent need for improved methods of treatment in the field of bone marrow transplants have led to the isolation of MSCs from bone marrow stroma. These MSCs are the same pluri-potential cells that result from expansion in Friedenstein type cultures. Several patents describe the isolation and therapeutic uses of these MSCs.

U.S. Pat. No. 5,486,359 to Caplan et al. is directed to isolated human MSCs, and a method for their isolation, purification, and culturing. Caplan et al. also describes methods for characterizing and using the purified mesenchymal stem cells for research, diagnostic, and therapeutic purposes. The invention in '359 to Caplan et al. describes pluri-potential cells that remain pluri-potential, even after cultural expansion. Caplan et al. also teaches that it is necessary to first isolate the pluri-potent MSCs from other cells in the bone marrow and then, in some applications, uses culture medium to expand the population of the isolated MSCs. This patent fails to disclose the use of Dexter-type cultures, pluri-differentiated mesenchymal progenitor cells, or the isolation of cells from Dexter-type cultures.

U.S. Pat. No. 5,733,542 to Haynesworth et al., is directed to methods and preparations for enhancing bone marrow engraftment in an individual by administering culturally expanded MSC preparations and a bone marrow graft. U.S. Pat. No. 6,010,696 to Caplan et al., is directed to methods and preparations for enhancing hematopoietic progenitor cell engraftment in an individual by administering culturally expanded MSC preparations and hematopoietic progenitor cells. The cells utilized in Haynesworth et al. and '696 to Caplan, et al. are the pluri-potential cells described in U.S. Pat. No. 5,486,359, above. Neither patent discloses the use of Dexter-type cultures, pluri-differentiated mesenchymal progenitor cells, or the isolation of cells from Dexter-type cultures.

Mesenchymal stem cells that are isolated from bone marrow are further described by Prockop (*Science*, 1997, 276(5309):71-4) and Pittenger et al. (*Science*, 1999, 284 (5411):143-147). These articles also describe pluri-potential but undifferentiated MSCs and fail to teach or disclose a pluri-differentiated mesenchymal cell or the isolation of mesenchymal cells from Dexter-type cultures.

While they may provide some benefit, the isolated MSCs in the prior art have not solved the problems associated with engraftment of hematopoietic progenitor cells or bone marrow engraftment. Consequently, there exists a need in the art for methods of improving engraftment of hematopoietic progenitor cells and engraftment of bone marrow in mammals in need of such treatment. There also exists a need in the art for treating and preventing the occurrence of GvHD in mammals that receive allogeneic bone marrow transplants.

BRIEF SUMMARY OF THE INVENTION

According to the present invention there is provided isolated pluri-differentiated mesenchymal progenitor cells, a method of isolation, diagnostic uses, and therapeutic uses relating to enhancing the engraftment of human bone marrow or hematopoietic progenitor cells and treating GvHD.

The present invention provides an isolated mesenchymal progenitor cell that is pluri-differentiated.

Accordingly, the present invention also provides a method for purifying pluri-differentiated mesenchymal progenitor cells including the steps of: providing a cell culture preparation by the Dexter method, treating the cells to obtain a cell suspension, removing macrophages, fractionating the cells, and collecting the fraction of pluri-differentiated mesenchymal progenitor cells.

The present invention also provides a method for enhancing bone marrow engraftment in a mammal in need thereof which includes administering to the mammal (i) isolated pluri-differentiated mesenchymal progenitor cells and (ii) a bone marrow graft, wherein the pluri-differentiated mesenchymal progenitor cells are administered in an amount effective to promote engraftment of the bone marrow in the mammal.

The present invention provides a method for enhancing engraftment of hematopoietic progenitor cells in a mammal in need thereof which includes the step of administering to the mammal (i) isolated pluri-differentiated mesenchymal progenitor cells and (ii) hematopoietic progenitor cells, wherein the pluri-differentiated mesenchymal progenitor cells are administered in an amount effective to promote engraftment of the hematopoietic progenitor cells in the mammal.

Another embodiment of the present invention provides a method for treating graft-versus-host disease (GvHD) in a mammal about to undergo bone marrow or organ transplantation or suffering from GvHD caused by bone marrow or organ transplantation, by administering to the mammal an effective amount of isolated pluri-differentiated mesenchymal progenitor cells.

Yet another embodiment of the present invention provides a method for diagnosing a disease state by: a) establishing gene expression patterns of normal state bone marrow derived isolated pluri-differentiated mesenchymal progenitor cells; b) establishing gene expression patterns of various leukemic state bone marrow derived isolated pluri-differentiated mesenchymal progenitor cells; c) identifying gene sets that are unique to a given state; and d) comparing a profile of bone marrow derived isolated mesenchymal progenitor cell of unknown state to the gene sets.

Additionally, the present invention provides a method for identifying therapeutic targets for treatment of hematopoietic function by: a) determining the median gene expression profile of bone marrow isolated pluri-differentiated mesenchymal progenitor cells associated with each disease state of interest; b) identifying gene groups that are up-regulated, down regulated, and common to each disease state; and c) identifying gene sets that are unique to a given state.

The present invention also includes therapeutic compositions including isolated pluri-differentiated mesenchymal progenitor cells and a pharmaceutically acceptable carrier, wherein the pluri-differentiated mesenchymal progenitor cells are present in an amount effective to enhance bone marrow engraftment in a mammal in need thereof; enhance hematopoietic progenitor cell engraftment in a mammal in need thereof; or treat GvHD in a mammal about to undergo bone marrow or organ transplantation or suffering from GvHD caused by bone marrow or organ transplantation.

BRIEF DESCRIPTION OF THE DRAWINGS

Other advantages of the present invention can be readily appreciated as the same becomes better understood by reference to the following detailed description when considered in connection with the accompanying drawings. The following is a brief description of the drawings which are presented only for the purposes of further illustrating the invention and not for the purposes of limiting same. Referring to the drawing figures, like reference numerals designate identical or corresponding elements throughout the several figures.

(FIG. 4B) Immunostain using anti-CD68 antibody (Immunotech, Clone PG-M1; Vector, Vectastain Elite ABC Kit). (FIG. 4C) Immunostain using anti-CD45 antibody (Dako, Clone PD7/26 & 2B11; ABC Kit). (FIG. 4D) Periodic acid-Schiff (Sigma). (FIG. 4E) Nile Red (Sigma), counterstained with DAPI (Vector). (FIG. 4F) Alkaline phosphatase (Sigma Kit No. 85), counterstained with Nuclear Fast Red (Baker). (FIG. 4G) Immunostain using antibody to fibronectin (Immunotech, Clone 120.5; ABC Kit). (FIG. 4H) Immunostain using anti-muscle actin antibody (Ventana, clone HUC 1-1; Ventana system using a section of formalin-fixed, paraffin-embedded cell block, instead of a cytospin). Appropriate positive controls and isotype-matched negative controls were employed to ascertain antibody staining-specificity. All parts of figure as shown, except FIGS. 4E and 4H, have clearly identifiable built-in cell controls. The morphological features of the cells are listed in row 1 of Table 1.

FIGS. 6A-6M represent different gene probes used for hybridization. The following outlines the sources of the gene probes employed and the approximate sizes of the major transcripts observed (shown in parentheses): FIG. 6A: CD68 (Clone ID 3176179, Genome Systems, Inc (GSI); 2-3 kb); FIG. 6B: Cathepsin B (Clone ID 2806166, GSI; 2-3 kb); FIG. 6C: GAPDH probe (generated using PCR primers from R&D Systems, Inc; ~2 kb) hybridized to same blot as A and B; FIG. 6D: Adipsin (probe generated using PCR primers as described, Ref 20; 0.5-1 kb); FIG. 6E: Osteoblast-specific cadherin-11 (Clone ID 434771, GSI; ~3 kb); FIG. 6F: Chondroitin sulfate proteoglycan 2 (Clone ID 1623237, GSI; >10 kb); FIG. 6G: Collagen type I alpha 1 (Clone ID 782235, GSI; >10 kb); FIG. 6H: Decorin (Clone ID 3820761, GSI; 2-3 kb); FIG. 6I: GAPDH probe hybridized to same blot as D-H; FIG. 6J: Fibronectin (Clone ID 3553729, GSI; >10 kb); FIG. 6K: Caldesmon (Clone ID 1319608, GSI; ~4 kb); FIG. 6L: Transgelin (Clone ID 4049957, GSI; ~1.5 kb); and FIG. 6M: GAPDH probe hybridized to same blot as J-L.

FIG. 9A shows CD45+/CD34+ progenitors in the marrow. FIG. 9B shows CD45/CD34-mature hematopoietic cells circulating in the blood.

FIGS. 10A-10H are photographs which show engraftment of human hematopoietic cells in a SCID mouse cotransplanted with the purified marrow MPCs of the present invention. FIG. 10A shows a serial section of a mouse spleen stained with H & E. FIG. 10B shows a serial section of a mouse spleen stained with immunoperoxidase stain for CD45. FIG. 10C shows bone marrow stained for CD45. FIG. 10D shows a serial section of the mouse liver stained with H&E depicting involvement of periportal areas. FIG. 10E shows a serial section of the mouse stomach stained with H&E showing transmural infiltration. FIG. 10F shows a serial section of the mouse lung stained with H&E showing involvement of peribronchial area. FIG. 10G shows a serial section of the mouse pancreas stained with H&E. FIG. 10H shows a serial section of the mouse paravertebral ganglia stained with H&E.

FIG. 12A shows that hybridization of sample DNA using a DNA probe specific for human chromosome 17 alpha satellite DNA (p17H8) results in a 2.7 Kb band (7) (arrow; autoradiogram exposed for only 45 minutes). FIG. 12B shows EcoR1 digest of thymic genomic DNA from SCID mice. FIG. 12C shows EcoR1 digest of lymph node genomic DNA from SCID mice.

FIGS. 13A-1, 13A-2, 13B-1, and 13B-2 show graphs comparing the survival rate and engraftment of human hematopoietic cells in SCID mice cotransplanted with the purified bone marrow MPCs of the present invention vs. unpurified bone marrow stromal cells. In the line graphs provided (FIGS. 13A-1 and 13B-1) the line with diamonds represents MPCs and bone marrow mononuclear cells, squares represents bone marrow mononuclear cells only, triangles represents unfractionated bone marrow stromal cells, the Xs represent MPCs only, and the circles represent the control. In the bar graphs (FIGS. 13A-2 and 13B-2), the gray bars represent mice that survived and the black bars represent mice with engraftment.

FIG. 14A shows a serial section of the liver of the mouse that survived. FIG. 14B shows a serial section of the liver of the mouse that died. FIG. 14C shows a serial section of the spleen of the mouse that survived.

DETAILED DESCRIPTION OF THE INVENTION

Generally, the present invention provides isolated and purified mesenchymal progenitor cells that are pluri-differentiated. Also provided by the present invention is a therapeutic composition including an effective amount of isolated and purified pluri-differentiated mesenchymal progenitor cells and a pharmaceutically acceptable carrier.

The present invention is premised upon the discovery that Dexter-type cultures contain stromal cells that co-express multiple message lineage markers. These pluri-differentiated cells are referred to by the inventor as mesenchymal progenitor cells (MPCs). Disclosed herein is a process for isolating and purifying MPCs from Dexter-type cultures. Purified MPCs provide a sufficiently defined system to permit detailed elucidation of the role of bone marrow in normal and leukemic hematopoiesis. The present invention is also directed to various methods for using MPCs to enhance bone marrow transplantation, enhance hematopoietic progenitor cell engraftment, for diagnostic purposes, or for the treatment of GvHD.

The term "pluri-differentiated" as used herein refers to cells that are a single cell type co-expressing genes specific for multiple lineages. The term "pluri-potential" as used herein refers to cells that are undifferentiated and have the potential to be differentiated into discrete mesenchymal tissues.

Dexter type bone marrow cultures are a widely used and favorite medium for the study of hematopoiesis. Conventional wisdom has held that the stromal cells in Dexter-type cultures comprise a mixture of macrophages, hematopoietic cells, adipocytes, osteoblasts, fibroblasts, muscle cells, and endothelial cells. As a result of this perceived cellular complexity, research efforts over the last 23 years were not directed to characterizing or isolating the mesenchymal cells from the Dexter-type cultures.

Figure 3:
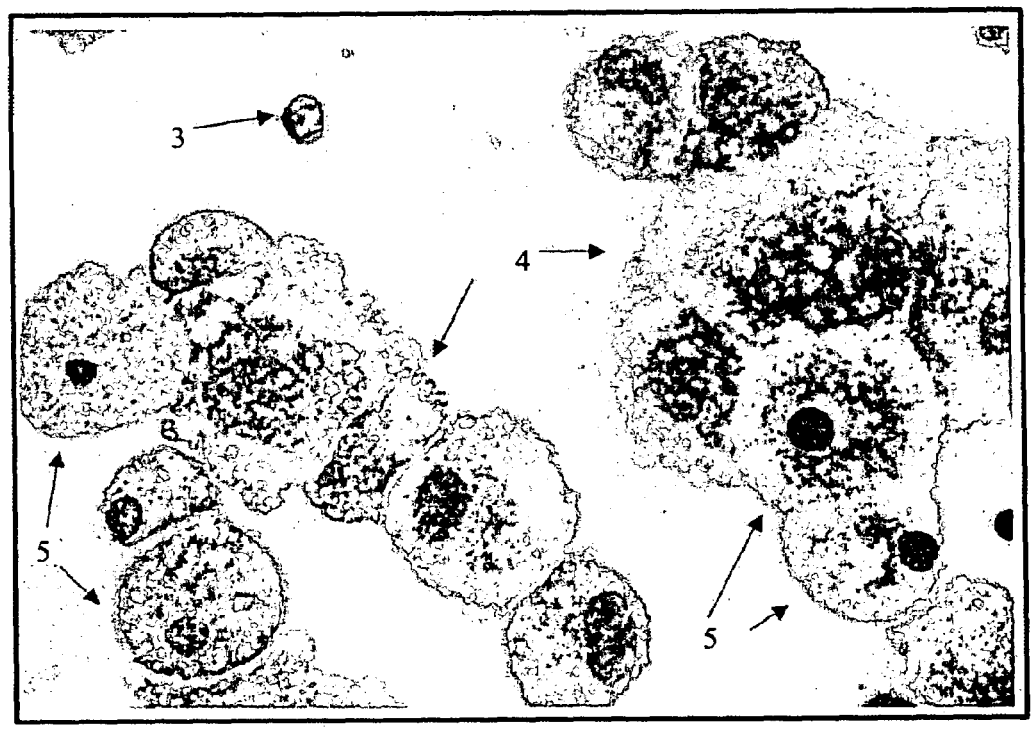
FIG. 3 is a photograph showing the Wright-Giemsa staining of Dexter-type stromacell cultures depicting three morphologically identifiable cell populations, macrophages (5), hematopoietic cells (3), and the mesenchymal progenitor cells (4) of the present invention.
Figure 4:
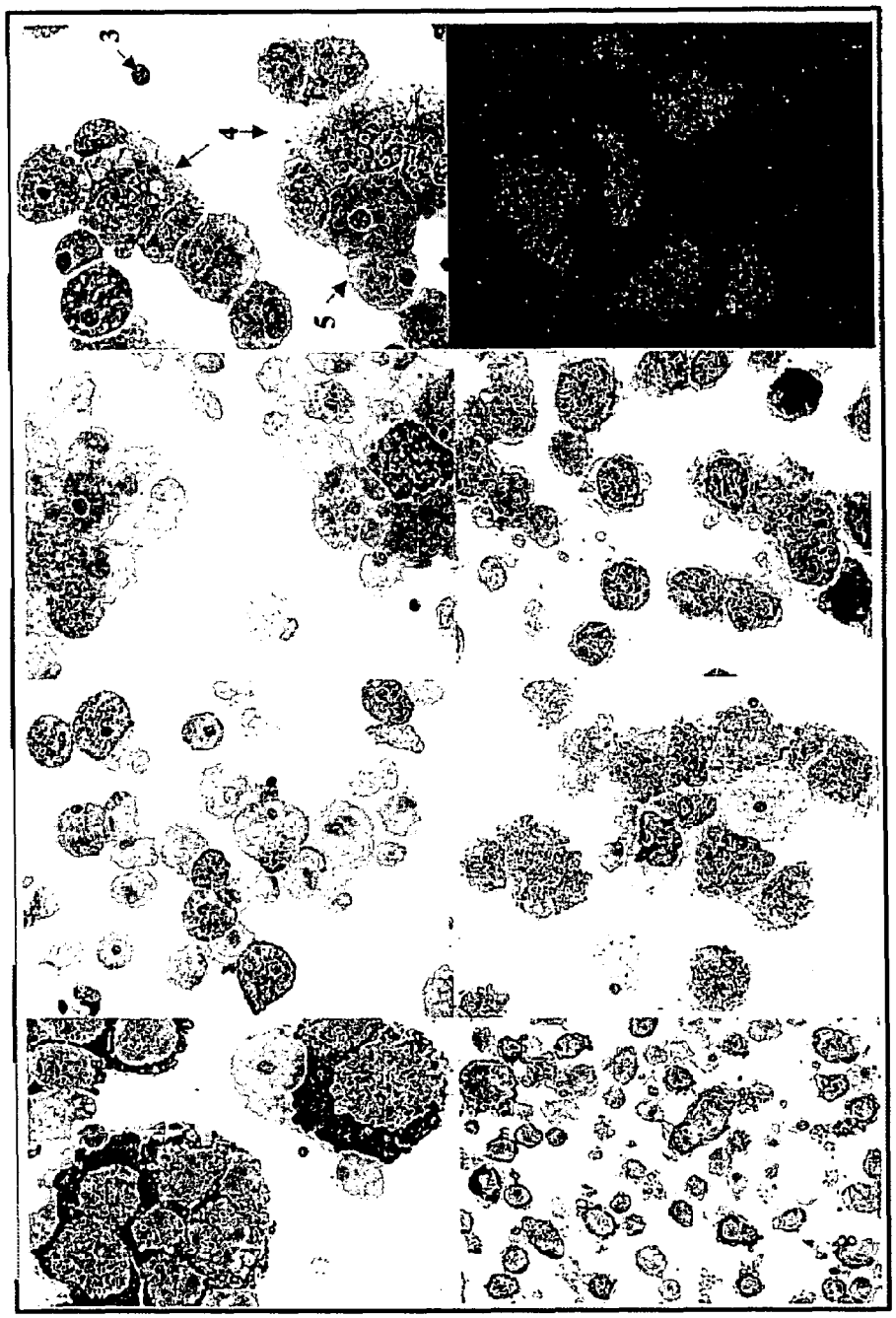
FIGS. 4A-4H are showing a series of photomicrographs showing the morphologic and phenotypic characteristics of the MPCs of the present invention, as uncovered by staining for representative mesenchymal cell lineage markers. The methods applied are shown in parentheses (FIG. 4A) Wright-Giemsa (Harleco stain using HMS Series Programmable Slide Stainer, Carl Zeiss, Inc.).
Figure 5:
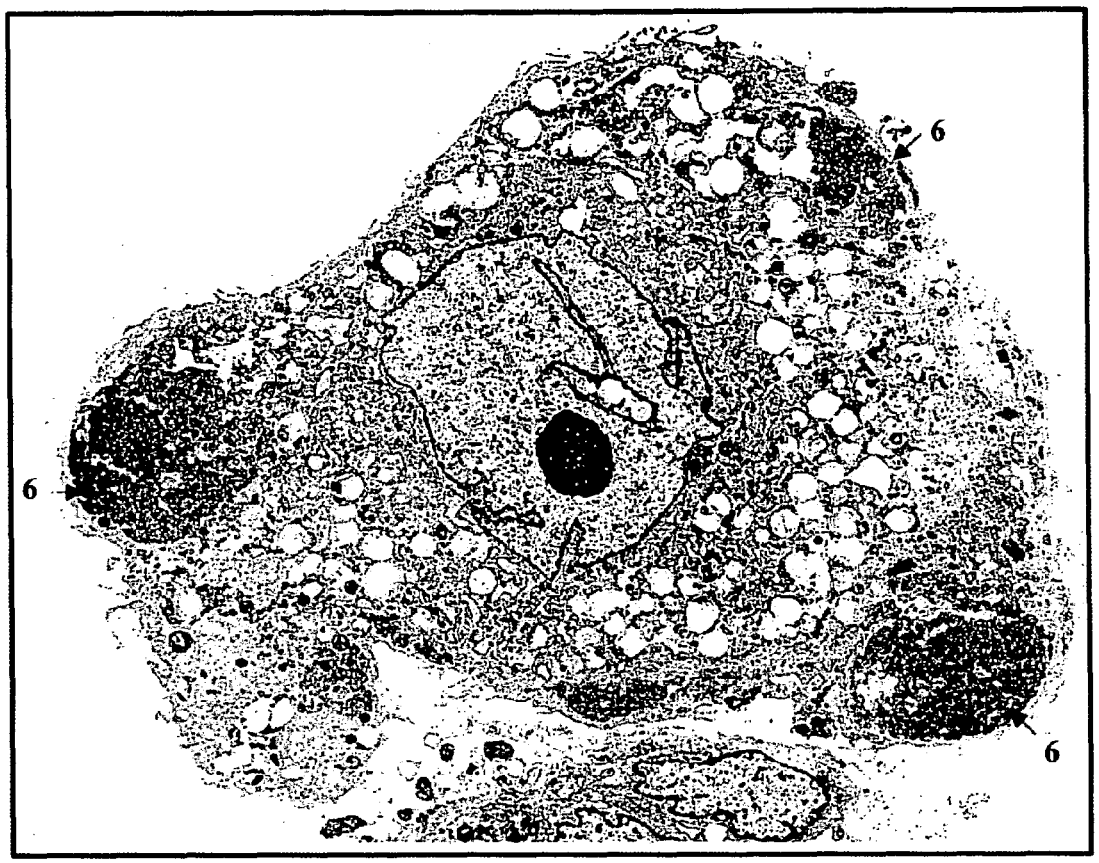
FIG. 5 is a photograph which shows a transmission electron micrograph of an MPC of the present invention bearing microvilli, irregular nucleus, and pools of glycogen (6) in the ectoplasm (×4,600).

Characterization of Cells. The exact cell types in Dexter cultures have been identified. No evidence was found for the existence of discrete cellular populations, such as adipocytes, osteoblasts, fibroblasts, smooth muscle cells and endothelial cells, notwithstanding the abundance of literature and wide spread belief (See, Liesveld, J. L. et al. *Blood*, 1989, 73:1794; Sullivan, A. K. et al. *Lab Invest*, 1989, 60:667; Dorshlind, K. *Ann Rev Immunol*, 1990, 8:126; Perkins, S. and Fleischman, R. A. *Blood*, 1990, 75:620; Denkers, I. A. et al. *Ann Hematol*, 1992, 64:210; Penn, P. E. et al. *Blood*, 1993, 81:1205; de Wynter, E. et al. *J Cell Sci*, 1993, 106:761; Ferrajoli, A. et al. *Stem Cells (Dayt)*, 1994, 12:638; Clark, B. R. and Keating, A. *Ann NY Acad Sci*, 1995, 770:70; Wilkins, B. S. and Jones, D. B. *Br J Haematol*, 1995, 90:757; Gronthos, S. and Simmons, P. J. *J Hematother*, 1996, 5:15; Soligo, D. et al. *Blood*, 94 (Supplement 1 (Part 2 of 2)):168b, Abstract #3926, Forty 1$^{st}$ Annual Meeting of the American Society of Hematology, New Orleans, La., Dec. 3-7, 1999; Dorheim, M-A. et al. *J Cell Physiol*, 1993, 154:317, Majumdar, M. K. et al. *J Cell Physiol.*, 1998, 176:57, Prockop, D. J. *Science*, 1997, 276: 71, Taichman, R. S. and Emerson, S. G. *J Exp Med*, 1994, 179:1677; Taichman, R. S. et al. *Blood*, 1996, 87:518; Verfaillie, C. M. in HEMATOLOGY: Basic Principles and Practice, R. Hoffman, et al., Eds., Churchill Livingstone, New York, 2000, pp. 140-142, Henderson, A. J. et al. *J Immunol*, 1990, 145:423; Long, M. W. et al. *J Clin Invest*, 1990, 86:1387; Simmons, P. J. et al. *Prog Clin Biol Res*, 1994, 389:271; Roecklein, B. A. and Torok-Storb, B. *Blood*, 1995, 85:997; Wineman, J. et al. *Blood*, 1996, 87:4082; Kelly, K. A. and Gimble, J. M. *Endocrinology*, 1998, 139: 2622; Hicok, K. C. et al. *J Bone Miner Res*, 1998, 13:205; Park, S. R. et al. *Bone*, 1999, 24:549; Dennis, J. E. et al. *J Bone Miner Res*, 1999, 14:700; and Torok-Storb, B. et al. *Ann NY Acad Sci*, 1999, 872:164). Instead, the inventor determined that there are only three types of cells in Dexter-type cultures, namely, macrophages (~35%), hematopoietic cells (~5%), and a type applicant calls "nonhematopoietic cells" (~60%) (FIG. 3, FIG. 4A, and Table 1).

Bone marrow mesenchymal cells, the nonhematopoietic cells in Dexter type cultures, possess distinctive features that have previously gone unrecognized. There is both direct visual (FIGS. 4A-4E and FIG. 5) and molecular biological (FIG. 6) evidence to support the existence of this unique cell type. These findings challenge the prevailing belief that stromal cells derived from Dexter cultures comprise multiple singly-differentiated mesenchymal cell types. Because Dexter cultures represent a primary cell culture system, and not a cell line, these studies indicate that cells in these primary cultures themselves are pluri-differentiated, which has been previously unsuspected. The nonhematopoietic cells of the present invention (MPCs) simultaneously express marker genes specific for multiple mesenchymal cell lineages, including adipocytes, osteoblasts, fibroblasts and smooth muscle cells.

The MPCs in Dexter type cultures were characterized using a variety of techniques. Cytospins were prepared using aliquots of unfractionated cells for performance of various cytological, cytochemical and immunocytochemical stains. Reactivity patterns of the bone marrow culture cells are outlined in Table 1. FIGS. 4A-4E illustrate morphologic and phenotypic characteristics, as uncovered by staining for representative cell lineage markers.

Only rarely have investigators in this field taken the approach of preparing a cell suspension and staining cells on cytospins as was done to characterize the cells of the present invention (Simmons et al. *Nature*, 1987, 328:429-432) and no other group has used this method to address the issue of pluri-differentiation by bone marrow stromal cells. Almost all of the published studies in the field, with a rare exception (Simmons et al. *Nature*, 1987, 328:429-432), conducted cytochemical and immunocytochemical staining on layers of stromal cells grown to confluence on coverslips. In this situation, the stromal cultures appear very complex especially in the areas of hematopoietic activity, the so-called "cobblestones" with macrophages and hematopoietic cells enmeshed in them. Macrophages and nonhematopoietic cells spread themselves and assume varied shapes when they adhere to and grow on plastic or glass that further contributes to the perceived heterogeneity and complexity. The complexity precludes a clear morphological visualization of the nonhematopoietic cells and consequently interfered with the determination of what percent of what cell type is positive for any given marker.

In terms of lineage markers, up to 100% of the nonhematopoietic cells or MPCs of the present invention expressed two fat cell markers (Nile Red (FIG. 4E) and Oil Red 0); an osteoblast marker (alkaline phosphatase (FIG. 4F)); and two fibroblast markers (fibronectin (FIG. 4G) and prolyl-4-hydroxylase). Greater than 85% of the MPCs were also positive for a muscle marker, actin (FIG. 4H). There was no evidence of expression of endothelial cell differentiation, as judged by immunohistochemical staining for CD34 and CD31.

In addition, the Dexter type stromal cells had not previously been subjected to Periodic acid-Schiff (PAS) staining, which revealed a strong and uniform positivity by almost 100% of the MPCs studied indicating the presence of large stores of glycogen (FIG. 4D). The presence of glycogen (6) was confirmed by electron microscopy (see FIG. 5). In this respect, MPCs are reminiscent of the glycogen-laden reticular cells in the developing bone marrow of human fetuses (observed by Chen, L-T. and Weiss, L. *Blood*, 1975, 46:389). Glycogen deposition is viewed to be a developmentally regulated process during morphogenesis (Ohshima, H. et al. *Cell Tissue Res.*, 1999, 297:271).

The MPCs also exhibited cytoplasm compartmentalization into endoplasm and ectoplasm. This morphologic finding sheds light on their internal architecture because of correlation of restricted localization of glycogen and smooth muscle actin to ectoplasm; and of acid phosphatase, alkaline phosphotase, Nile Red, Oil Red 0, fibronectin, and prolyl-4-hydrolase to endoplasm.

Additional sets of multiple mesenchymal lineage markers were assessed by Northern blotting of unfractionated cells and purified MPCs to eliminate any observer bias that might be inherent in morphological assessment. FIGS. 6A-6M represent different gene probes used for hybridization. The sources of the gene probes employed and the major transcripts observed are outlined in the brief description of the figures.

Compared to unfractionated cells, the purified nonhematopoietic cells expressed significantly higher levels of markers representing fat cells (adipsin, FIG. 6D); osteoblasts (osteoblast-specific cadherin-11, chondroitin sulfate, collagen type 1 and decorin, FIGS. 6E-6H); fibroblasts (fibronectin, FIG. 6J); and smooth muscle cells (caldesmon and transgelin, FIGS. 6K-6L).

Taken together, the morphologic, cytochemical, and immunocytochemical results (FIGS. 4A-4H and Table 1), and the Northern blotting data (FIGS. 6A-6M) indicate that the nonhematopoietic stromal cells of the Dexter cultures co-express markers specific for at least four different mesenchymal cell lineages. Using a variety of techniques, applicant has demonstrated that the MPCs co-express multilineage mesenchymal cell phenotypes, and in this respect the multi- or pluri-differentiated MPCs are distinct from the pluri-potential, but undifferentiated, MSCs of Friedenstein cultures (Prockop, *Science*, 1997, 276:71-74).

Figure 2:
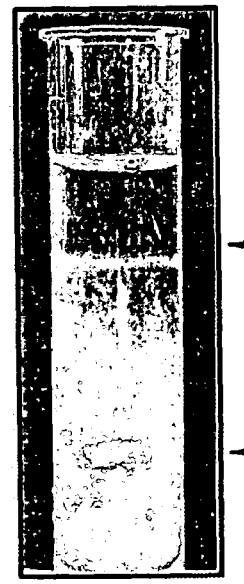
FIG. 2 is a photograph showing the percoll gradient centrifugation technique of the present invention that purifies the MPCs (2) in large quantities to greater than 95% purity.

Isolation of MPCs. The nonhematopoietic cells of the present invention were purified from the macrophages, the dominant "contaminating" cell type, using a Percoll gradient method developed by applicant. MPCs were purified by the following process: cells from a Dexter-type culture were treated to obtain a cell suspension, the macrophages were removed, and the cells were fractionated using discontinuous Percoll gradient centrifugation (FIG. 2). The isolated MPCs were then collected and washed.

The purity of the nonhematopoietic cells was demonstrated by a near complete absence of two macrophage markers, CD68 and cathepsin B (as shown by Northern blotting data, FIGS. 6A and 6B). As a positive control, bone marrow mononuclear cells rich in myelomonocytic cells abundantly expressed CD68 (lanes 5 & 6, FIG. 6A). The Northern blot results are consistent with a purity estimate of ~95% (vs. 60% in unfractionated samples) based on morphology and immunocytochemical staining for CD68.

A purified source of MPCs is desirable for a number of reasons. The relative ease with which large numbers of the MPCs can be purified and their distinctive phenotypic characteristics make them valuable targets for future investigations. Purified MPCs provide a sufficiently defined system to permit detailed elucidation of the role of bone marrow in normal and leukemic hematopoiesis in addition to aiding in bone marrow transplantation.

Another major reason that purified cells are desirable is that Dexter cultures also contain a significant percentage of highly immunogenic macrophages that can cause onset of GvHD after transplantation. The MPCs of the present invention are purified to ~95% free of macrophages and hematopoietic cells. Note the increased survival rate in SCID mice that received purified MPCs versus those that received unfractionated bone marrow stromal cells in FIGS. 13B-1 and 13B-2.

Figure 7:
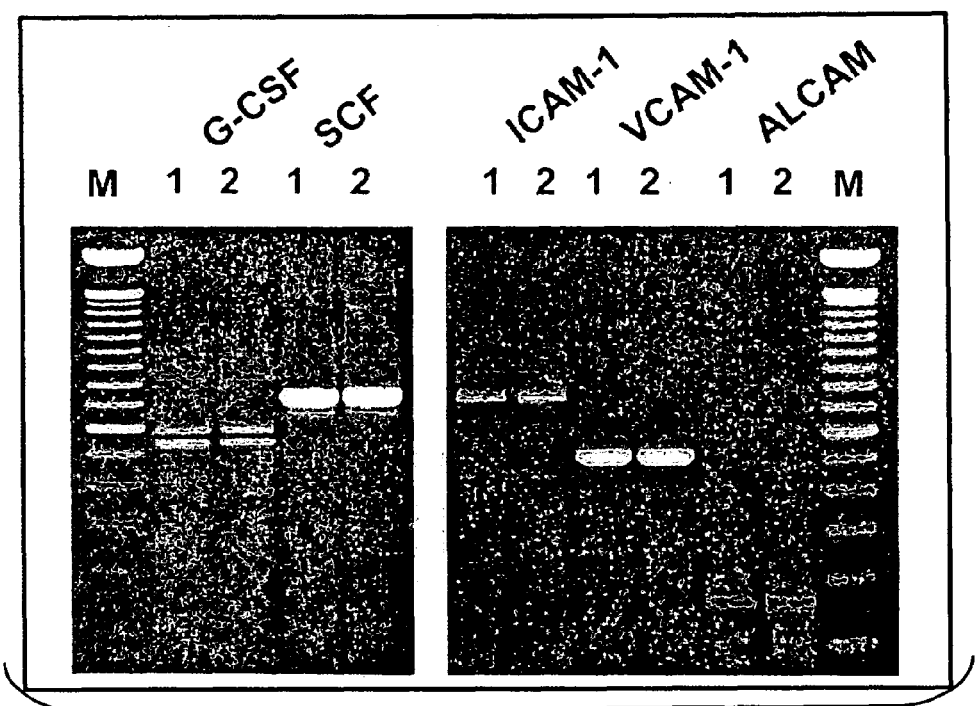
FIG. 7 is a photograph which shows RT-PCR analysis for expression of representative hematopoietic growth factors (G-CSF and SCF) and extracellular matrix receptors (ICAM-1, VCAM-1, and ALCAM) by the MPCs of the present invention.

Enhancing Engraftment. The present invention also provides methods of enhancing the engraftment of hematopoietic cells and of enhancing the engraftment of bone marrow. The hematopoietic support capacity of the Dexter-type cultures has been repeatedly demonstrated by a number of investigators. RT-PCR analysis showed that Dexter cultures and Friedenstein cultures expressed a similar pattern of cytokine and growth factor mRNAs; yet, Dexter cultures were found to be more efficient than Friedenstein cultures in achieving preservation of hematopoietic progenitors (Majumdar et al. *J. Cell. Physiol.*, 1998, 176:57-66). The pluri-differentiated MPC is capable of supporting hematopoiesis, as shown by its ability to express representative hematopoietic growth factors/cytokines, i.e., G-CSF and SCF as well as matrix receptors/hematopoietic cell adhesion molecules, i.e., ICAM-1, VCAM-1 and ALCAM (FIG. 7).

Clarification of the nature of the stromal cells and the ability to purify these cells makes it possible to use them as an adjuvant in bone marrow transplantation following high-dose chemotherapy and radiation therapy. These treatment modalities not only cause damage to the hematopoietic stem cells but also to the supportive stromal cells. However, because the bone marrow microenvironment is destroyed, hematopoietic progenitor cell engraftment is delayed until the stromal environment is restored. As a result, a critical aspect of the current invention is directed to the advantages of transplanting isolated mesenchymal progenitor cells to accelerate the process of stromal reconstruction and ultimately bone marrow engraftment. The stromal cells present in the standard bone marrow transplant are not sufficient in number and can be supplemented with the cultured MPCs of the present invention.

Yet another embodiment of the current invention provides the use of MPC transplantation to major leukemic conditions, such as acute myeloid leukemia (AML), myelodysplastic syndromes (MDS), chronic myeloid leukemia (CML) and multiple myeloma (MM). This is based on applicant's determination that bone marrow stromal cells in a leukemia patient are functionally and structurally defective, regardless of the damage caused by chemotherapy and radiation therapy. Such defects in bone marrow stromal cells are likely to aid and abet leukemia development. Alternatively, stromal cell defects could be secondarily induced by surrounding leukemia cells, thus contributing to the loss of hematopoietic support function of stromal cells and hematopoietic failure, which is an invariable feature in leukemia. Regardless whether the observed stromal cell defects are primary or secondary to the leukemic process, by reason of their indisputable impact on normal hematopoiesis, these defects remain to be corrected to improve the hematopoietic function.

Stromal cells have never been carefully investigated in terms of genomics in view of the widespread belief that they represent a heterogeneous mixture of cell types. Tissue or cellular heterogeneity presents a major challenge for the application of microarray technology. The purified stromal cells of the present invention represent a single pluridifferentiated MPG which allows for genomic study of the stromal cells and the development of new, more objective diagnostic tools for patients suffering from leukemia conditions.

The ability to purify culture-expanded MPCs from both normal individuals and patients afflicted with various leukemias also allows testing of the hematopoietic supportive role of MPCs in mice models. These systems provide an in vivo model in which to examine the role of human bone marrow microenvironment in normal and leukemic hematopoiesis.

The Severe Combined Immunodeficiency Disease (SCID) mouse model is an ideal system in which to investigate MPC function. Engraftment of human hematopoietic progenitors in SCID mice has required either coadministration of exogenous human cytokines, or cotransplantation of human bone marrow plugs or bone fragments. As disclosed herein MPCs are a convenient, new source for human bone marrow stromal cells for enhancing transplantation that does not require cytokines, bone fragment, or marrow.

Unlike prior methods, the isolated MPCs of the present invention support human hematopoiesis in the SCID mouse model as effectively as whole marrow stroma. The transplantation of human marrow mononuclear cells combined with purified MPCs results in dramatically vigorous engraftment of human cells in spleen, bone marrow, liver, pancreas, lungs, stomach, and paravertebral neuronal ganglia of SCID mice (FIGS. 10A-10H and FIGS. 11A-11C). By contrast, mice receiving human bone marrow mononuclear cells alone or MPCs alone expectedly showed no detectable evidence of human hematopoietic cell engraftment (FIGS. 13A-1, 13A-2, 13B-1, and 13B-2).

GvHD. The present invention also provides for a method of preventing or treating GvHD. The highest mortality rate, FIGS. 13B-1 and 13B-2, was observed in mice receiving the unpurified whole marrow stroma and the bone marrow mononuclear cells. The increased mortality observed is related to the presence of highly immunogenic macrophages and consequent GvHD. The mice with the highest survival rate, shown in FIGS. 13A-1 and 13A-2, were the mice receiving purified MPCs and bone marrow mononuclear cells.

Figures 14A, 14B:
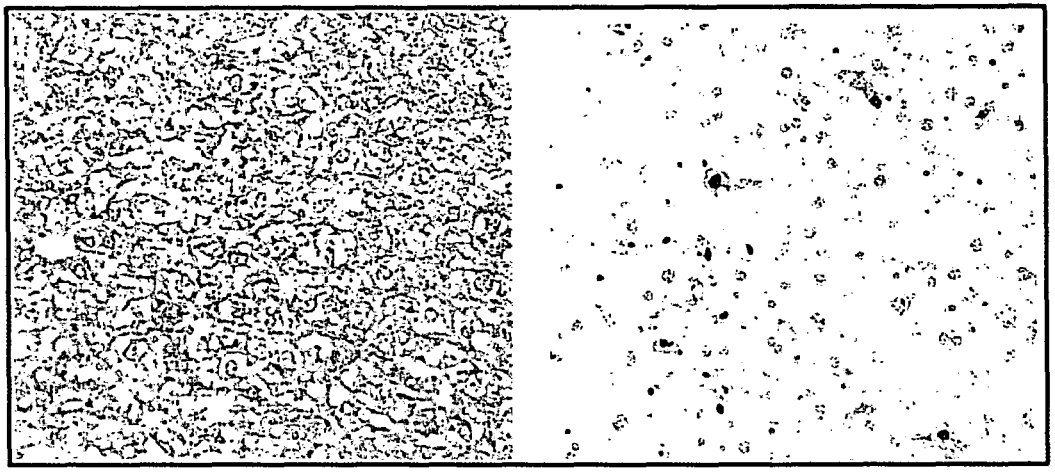
FIGS. 14A-14C are photographs which demonstrate apoptosis by TUNEL assay in organs of SCID mice that died after transplantation.
Figures 14C, 14D:
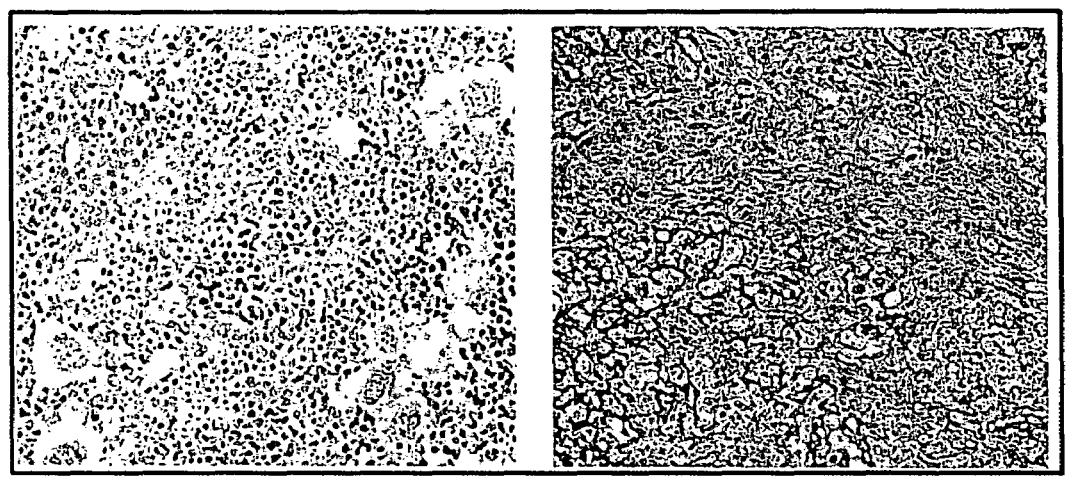
FIG. 14D shows a serial section of the spleen of the mouse that died.

Notably, there is discrete TUNEL-positive nuclei in the liver of the expired mouse in FIG. 14B and complete absence of staining in the liver of the surviving mouse (see FIG. 14A). While some ill-defined globules of staining are observed in the spleen of the mouse that survived, the nuclear integrity of most of the cells is well preserved suggesting minimal or no apoptosis (FIG. 14C). In contrast, the dead mouse spleen (FIG. 14D) showed extensive TUNEL positivity precluding accurate interpretation. Control mouse liver and spleen showed results similar to those of the mouse that survived.

The above results indicate that purified MPCs can support human hematopoiesis in SCID mice as effectively as whole marrow stroma. Equally important is that the purified MPCs increased the survival rate. The evidence shows that the increased survival is due to a reduction in GvHD.

Allogeneic bone marrow transplantation is the preferred method of treatment for a variety of malignant and genetic diseases of the blood and blood forming cells. However, failure of hematopoietic cell engraftment can occur for a number of reasons. These include, microenvironmental defects as part of the underlying disease itself (e.g., aplastic anemia), and/or stromal cell damage caused by chemoradiotherapy and/or microenvironmental damage as part of GvHD which is a dreaded complication following bone marrow transplantation. In GvHD, donor T cells present in the hematopoietic cell graft destroy host tissues. GvHD can involve multiple organs such as skin, liver, GI system etc. The current treatment modalities for graft failure or GvHD are cumbersome, costly and involve some form of immunosuppression. Stromal cell lesions either primary to the disease process or secondarily induced by allogeneic bone marrow transplantation play a prominent role in the success or failure of the hematopoietic cell graft. Cotransplantation of MPC not only enhances hematopoietic cell engraftment but also prolongs the life of graft recipients by minimizing GvHD. Co-transplantation of healthy, culture-expanded MPC is a viable option in these situations.

The human bone marrow used in the Dexter-type cultures of the present invention can be obtained from a number of different sources in accordance with the procedures known in the art, including from plugs of femoral head cancerous bone pieces or from aspirated marrow. The cells used in the Dexter culture can be autologous, from the tissue donor, or from other individuals.

Modes of administration of MPCs include, but are not limited to, systemic intravenous injection and injection directly to the intended site of activity. The MPCs can be administered by any convenient route, for example by infusion or bolus injection, and can be administered together with other biologically active agents. Administration is preferably systemic.

The methods of the present invention can be altered, particularly by (1) increasing or decreasing the time interval between administering MPCs and implanting the tissue, cells, or implanting the organs; (2) increasing or decreasing the amount of MPCs administered; (3) varying the number of MPC administrations; (4) varying the method of delivery of the MPCs; (5) or varying the source of MPCs.

The MPC preparations are used in an amount effective to promote engraftment of hematopoietic progenitor cells or bone marrow cells; or for the treatment or prevention of GvHD in the recipient. The pharmaceutically effective amount for the purposes herein is thus determined by such considerations as are known in the art. In general, such amounts are typically at least $1 \times 10^4$ MPCs per kg of body weight and most generally need not be more than $7 \times 10^5$ MPCs/kg.

The present invention also provides pharmaceutical compositions. Such compositions comprise a therapeutically effective amount of MPCs and a pharmaceutically acceptable carrier or excipient. Such a carrier includes but is not limited to McCoy's medium, saline, buffered saline, dextrose, water, and combinations thereof. The formulation should suit the method of administration.

In one embodiment, the MPC preparation or composition is formulated in accordance with routine procedures as a pharmaceutical composition adapted for intravenous administration to human beings. Typically, compositions for intravenous administration are solutions in sterile isotonic aqueous buffer. Where necessary, the composition can also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The present invention paves the way for applications of mesenchymal progenitor cells in the field of transplantation with respect to hematopoietic support, immunoregulation, and graft facilitation. MPCs can be used as a supporting cell type in bone marrow transplantation, particularly in diseases where defects in the hematopoietic stromal microenvironment are believed to prevail, such as aplastic anemia, myelofibrosis, and bone marrow failure following high dose chemotherapy and radiation therapy.

Diagnostic Applications. Another aspect of the invention provides a method for diagnosing various disease states in mammals by identifying new diagnostic markers, specifically the classification and diagnosis of leukemia. Prior to the present invention, stromal cells were not carefully investigated in terms of genomics because of the widespread belief that they represent a heterogeneous mixture of cell types and cellular heterogeneity presents significant challenges for the application of genetic analysis such as microarray technology. The isolated MPCs of the present invention represent a single cell type and allow for genomic study of the stromal cells.

Using the methods of the present invention, it has been determined that bone marrow stromal cells in leukemia patients are functionally and structurally defective regardless of the damage caused by chemotherapy and radiation therapy. Given the almost 25 year history and intense interest in bone marrow stromal cell cultures, previous documentation of stromal cell abnormalities has been disappointingly low (Martinez & Martinez, *Exp. Hematol*, 1983, 11:522-526; Budak-Alpdogan et al. *Am. J. Hematol*, 1999, 62:212-220; Nagao et al. *Blood*, 1983, 61:589-592; Peled et al. *Exp. Hematol*, 1996, 24:728-737; Bhatia et al. *Blood*, 1995, 85:3636-3645; Agarwal et al. *Blood*, 1995, 85:1306-1312; Diana et al. *Blood*, 2000, 96:357a). By identifying gene sets that are unique to a given state, these differences in the stromal cells can be utilized for diagnostic purposes.

In one embodiment of the invention, isolated MPCs from a patient are assayed for expression of a large number of genes. The gene expression profile is projected into a profile of gene set expression values according to the definition of gene sets. A reference database containing a number of reference projected profiles is also created from the isolated MPCs of patients with known states, such as normal and various leukemic disease states. The projected profile is then compared with the reference database containing the reference projected profiles. If the projected profile of the patient matches best with the profile of a particular disease state in the database, the patient is diagnosed as having such disease state. Various computer systems and software, see Example 5, can be utilized for implementing the analytical methods of this invention and are apparent to one of skill in the art.

Some of these software programs include Cluster & TreeView (Stanford), GeneCluster (MIT/Whitehead Institute), Array Explorer (SpotFire Inc) and GENESPRING (Silicon Genetics Inc) (for computer systems and software, see also U.S. Pat. No. 6,203,987).

The methods of the present invention can also be useful for monitoring the progression of diseases and the effectiveness of treatments. For example, by comparing the projected profile prior to treatment with the profile after treatment.

Therapeutic Applications. One aspect of the invention provides methods for therapeutic and drug discovery utilizing bone marrow derived isolated mesenchymal progenitor cells. The present invention can be utilized to identify stromal cell genes that can be therapeutic targets for improvement of normal hematopoietic function, which is constantly compromised, in leukemic patients. In one embodiment, gene sets are defined using cluster analysis. The genes within a gene set are indicated as potentially co-regulated under the conditions of interest. Co-regulated genes are further explored as potentially being involved in a regulatory pathway. Identification of genes involved in a regulatory pathway provides useful information for designing and screening new drugs.

Some embodiments of the invention employ gene set definition and projection to identify drug action pathways. In one embodiment, the expression changes of a large number of genes in response to the application of a drug are measured. The expression change profile is projected into a gene set expression change profile. In some cases, each of the gene sets represents one particular pathway with a defined biological purpose. By examining the change of gene sets, the action pathway can be deciphered. In some other cases, the expression change profile is compared with a database of projected profiles obtained by perturbing many different pathways. If the projected profile is similar to a projected profile derived from a known perturbation, the action pathway of the drug is indicated as similar to the known perturbation. Identification of drug action pathways is useful for drug discovery. See, Stoughton and Friend, Methods for Identifying pathways of Drug Action, U.S. patent application Ser. No. 09/074,983.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

The examples presented in this experiment can be summarized as follows. The data disclosed herein demonstrate that Dexter cultures consist of only three cell types macrophages (~35%), hematopoietic cells (~5%), and nonhematopoietic cells (~60%). Using a percoll gradient centrifugation technique, the nonhematopoietic mesenchymal progenitor cells were isolated, free of macrophages and hematopoietic cells. A variety of techniques were used to identify the isolated cells as a multi-differentiated mesenchymal cell lineage co-expressing genes specific for multiple mesenchymal cell lineages including adipocytes, osteoblasts, fibroblasts and muscle cells.

Evidence that this multi- or pluri-differentiated mesenchymal progenitor cell is capable of supporting hematopoiesis is shown by the expression of a number of hematopoietic growth factors and extracellular matrix receptors. The SCID mouse experimental data provides evidence that since the MPCs can be purified to near homogeneity (95%) with relative ease, MPCs can be of value for enhancing engraftment of hematopoietic stem cells and bone marrow transplants. Additionally, increased survival rate in the SCID mouse model indicates that isolated MPCs can also be useful for the treatment of GvHD. An example of the administration of bone marrow cells and MPCs to breast cancer patients treated with chemotherapy is also provided.

A stepwise genomics strategy and an example of the genomic changes observed in leukemia associated MPCs is also provided. Cluster analysis was performed to show gene expression patterns in isolated MPCs of a normal individual and individuals with different leukemic conditions. The approach presented provides the basis for a new more objective means to diagnose patients suffering from leukemic conditions.

Example 1

Isolation and Characterization of MPCs from Dexter-Type Bone Marrow Stromal Cell Culture Systems Bone Marrow Culture: Bone marrow samples were obtained from posterior superior iliac crest under general anesthesia for standard marrow transplantation. Marrow stromal cell cultures were set up using the residual cells recovered from the filters of Fenwal Bone Marrow Collection System after complete filtration of the marrow samples. The filters were rinsed with phosphate-buffered saline without $Ca^{2+}$ and $Mg^{2+}$ (PBS-CMF). The cell suspension was subjected to Ficoll gradient isolation of the mononuclear cells (bone marrow MNCs). The bone marrow MNCs were washed (×2) in PBS-CMF and suspended in McCoy's 5A with HEPES medium containing 12.5% fetal bovine serum (FBS), 12.5% horse serum, 1 µM/L hydrocortisone and 1% penicillin/streptomycin (for this study McCoy's complete medium) and cultured under standard stromal-cell culture conditions (FIG. 1) (Seshi et al. *Blood*, 1994, 83:2399; Gartner et al. *Proc Natl Acad Sci USA*, 1980, 77:4756). After two weeks, confluent stromal cell cultures were trypsinized (first passage), followed by splitting each T75 flask into two T150 flasks.

Morphologic and Phenotypic Characteristics of MPCs as Uncovered by Staining for Representative Mesenchymal Cell Lineage Markers: Two weeks after the first passage (above), confluent stromal cells were again trypsinized. Cytospins were prepared using aliquots of unfractionated cells for performance of various cytological, cytochemical and immunocytochemical stains.

Reactivity patterns of the bone marrow culture cells are outlined in Table 1. FIGS. 4A-4E illustrate morphologic and phenotypic characteristics, as uncovered by staining for representative cell lineage markers. As illustrated in Table 1 and FIGS. 3 and 4A, Wright-Giemsa staining revealed three morphologically identifiable cell populations in Dexter type stromal cell cultures, macrophages, hematopoietic cells, and nonhematopoietic cells (labeled 4, 3, and 5, respectively).

The identity of macrophages was confirmed by immunostain using anti-CD68 antibody (FIG. 4B) and cytochemical stains for acid phosphatase and Sudan black. The identity of hematopoietic cells (including macrophages) was confirmed by immunostain using anti-CD45 antibody (FIG. 4C).

The remaining nonhematopoietic cells stained intensely positive for Periodic acid-Schiff, which was diastase sensitive, signifying the presence of large stores of glycogen (FIG. 4D). The presence of glycogen (6) was confirmed by electron microscopy (see FIG. 5). In this respect, MPCs are reminiscent of the glycogen-laden reticular cells in the developing bone marrow of human fetuses (observed by Chen, L-T. and Weiss, L. *Blood*, 1975, 46:389). Glycogen deposition is viewed to be a developmentally regulated process during morphogenesis (Ohshima, H. et al. *Cell Tissue Res.*, 1999, 297:271).

In terms of lineage markers, up to 100% of the nonhematopoietic cells expressed two fat cell markers (Nile Red (FIG. 4E) and Oil Red O); an osteoblast marker (alkaline phosphatase (FIG. 4F)); and two fibroblast markers (fibronectin (FIG. 4G) and prolyl-4-hydroxylase). Greater than 85% of the nonhematopoietic cells were also positive for a muscle marker, actin (FIG. 4H). There was no evidence of expression of endothelial cell differentiation, as judged by immunohistochemical staining for CD34 and CD31 (data not shown).

The results indicate that the nonhematopoietic cells of the Dexter cultures are in fact a single, pluri-differentiated cell type co-expressing multiple mesenchymal cell lineage markers. The pluri-differentiated mesenchymal progenitor cells reported here are to be distinguished from the pluripotential, but undifferentiated, MSCs that are generated in the absence of hematopoietic cells, such as in Friedenstein-type cultures.

TABLE 1

Reactivity patterns of bone marrow stromal cells based on cytological, cytochemical and immunocytochemical stains*,***

| FIG. | Test Utilized | Macrophages | Hematopoietic Cells | Mesenchymal Progenitor Cells |
| --- | --- | --- | --- | --- |
| 1 3 and 4A | Wright-Giemsa (Harleco) | Large cells with a small round nucleus & foamy cytoplasm: 35% of total cells | Small cells with minimal amount of cytoplasm: 5% of total cells | Large cells with a relatively irregular nucleus & cytoplasm compartmentalized into ectoplasm and endoplasm: 60% of total cells |

TABLE 1-continued

Reactivity patterns of bone marrow stromal cells based on cytological, cytochemical and immunocytochemical stains*,***

| FIG. | | Test Utilized | Macrophages | Hematopoietic Cells | Mesenchymal Progenitor Cells |
|---|---|---|---|---|---|
| 2 | 4D | Periodic acid-Schiff (PAS) (Sigma) | 0 | 0 | ~100% MPCs: staining restricted to ectoplasm in a ring-like fashion; and completely abolished by diastase digestion |
| 3 | 4C | CD45 (Dako, PD7/26 & 2B11) | 100% macrophages (MΦ) | 100% HCs | 0 |
| 4 | 4B | CD68 (Immunotech, clone PG-M1) | 100% MΦ | 0 | 0 |
| 5 | | Sudan Black (Sigma) | ~100% MΦ | 0 | 0 |
| 6 | | Acid phosphatase (Sigma Kit No. 387) | 100% MΦ; positive granules packed throughout cytoplasm | 0 | 100% MPCs; positive granules in moderate amounts; staining restricted to endoplasm |
| 7 | 4E | Nile Red (Sigma) | 0 | 0 | ~100% MPCs: staining restricted to endoplasm |
| 8 | | Oil Red O (Sigma) | 0 | 0 | ~100% MPCs: staining restricted to endoplasm |
| 9 | 4F | Alkaline phosphatase (Sigma Kit No. 85) | 0 | 0 | ~100% MPCs: variable number of positive granules; staining restricted to endoplasm & plasma membrane** |
| 10 | 4G | Fibronectin (Immunotech, clone 120.5) | 0 | 0 | ~100% MPCs: staining restricted to endoplasm |
| 11 | | Prolyl-4-hydroxylase (Dako, clone 5B5) | 0 | 0 | ~100% MPCs: staining preferentially in the endoplasm |
| 12 | 4H | Muscle actin (Ventana, clone HUC 1-1) | 0 | 0 | >85% MPCs: variable staining restricted to ectoplasm |

*The lineages of the markers tested above are: 3, hematopoietic cell marker; 4, 5 and 6, monocyte/macrophage markers; 7 and 8, adipocyte markers; 9, osteoblast marker; 10 and 11, fibroblast markers; 12 muscle marker.
**One earlier study (Simmons et al. Nature, 1987, 328: 429–432) interpreted the localization of alkaline phosphatase staining as confined to the plasma membrane when in fact it is predominately present within the endoplasm (compare FIG. 1C of this reference with FIG. 4F).
***While well-accepted mesenchymal lineage markers were used, these markers do not necessarily lend themselves to simultaneous assessment of the same cell. For example, muscle-specific actin antibody worked only on formalin-fixed, paraffin embedded material, whereas stains like alkaline phosphatase, Oil Red and Nile Red are not anti-body based and involve varying fixing and staining conditions. Thus, the evidence shows that close to 100% of members of a morphologically distinct population # express multiple lineage markers of interest.

Bone Marrow Mesenchymal Progenitor Cell (MPC) Purification: To further investigate the characteristics of the MPCs, the nonhematopoietic stromal cells were then purified from the macrophages (~95% pure), the dominant "contaminating" cell type using the following method. Confluent monolayers of stromal cells resulting from first passage, above, were washed for three minutes in $Ca^{2+}/Mg^{2+}$ free Hanks' balanced salt solution. Cells were incubated at room temperature for 45 minutes with intermittent mixing in serum-free McCoy's medium containing 10 mM L-leucine methyl ester (LME, Sigma). LME is a lysosomotropic agent that selectively kills and detaches macrophages. The detached macrophages were removed by washing the monolayers twice in McCoy's complete medium, followed by trypsinization of the monolayers. The resulting single cell suspensions were fractionated by discontinuous Percoll gradient (70%, 50%, 30%, 20%, 10%) centrifugation at 800×G for 15 minutes at 4° C. in a fixed angle rotor (Avanti-J25

Beckman centrifuge) (FIG. 2). Low-density cells representing the macrophages resistant to detachment by LME separate as a band at the interface of serum and 10% Percoll and were discarded (1). High-density nonhematopoietic cells representing MPCs form a layer in the region of 30-50% Percoll (2). These were collected and washed twice by centrifugation through PBS-CMF. This protocol is conservatively expected to yield, >2.5×10⁶ MPCs per T-150 flask (i.e., >50×10⁶ MPCs per batch of 20 flasks). The purity of these preparations, typically about 95%, was routinely monitored by Wright-Giemsa staining.

Northern Blotting: Additional sets of multiple mesenchymal lineage markers were assessed by Northern blotting to eliminate any observer bias that might be inherent in morphological assessment. FIGS. 6A-6M represent different gene probes used for hybridization. The sources of the gene probes employed and the major transcripts observed are outlined in the brief description of the figures.

Total RNA was prepared by dissolving the high-density cell pellets in Trizol (Life-Technologies). Total RNA samples from unfractionated stromal cells and BM MNCs were similarly prepared. The RNA samples were electrophoresed in a standard 1% agarose gel containing 2% formaldehyde in MOPS/EDTA buffer and blotted onto Immobilon-Ny+ membrane. Probes were labeled using Prime-A-Gene Kit (Promega) and a.sup.32P dCTP (NEN). Hybridization was performed at 65° C. in modified Church's hybridization solution using 3×10⁶ counts/ml in 10 ml (Millipore, 1998).

In FIGS. 6A-6M, Northern blot analysis was performed side-by-side on fractionated stromal cells, nonhematopoietic cells freed of macrophages, and initial bone marrow mononuclear cell samples. Lanes 1 and 2 represent total RNA samples (10 μg each) from unfractionated stromal cells (subjects S1 and S2, respectively). Lanes 3 and 4 represent total RNA samples (10 μg each) from purified stromal MPCs (subjects S1 and S2, respectively). Lanes 5 and 6 represent total RNA samples (10 μg each) from bone marrow mononuclear cells, the starting cells for bone marrow cell cultures (subjects S3 and S4, respectively).

The large transcripts, especially of collagen (lane 1, FIG. 6G) and fibronectin (lane 1, FIG. 6J), in RNA extracted from unfractionated stromal cells of subject 1 showed difficulty migrating into the gel. This observation correlates with the presence of an artifact of unresolved positive material in lane 1, FIG. 6A. Since the RNA extracted from unfractionated stromal cells of the subject 2 did not present this problem (lane 2, FIG. 6G, FIG. 6J, and FIG. 6A), the observation does not impact on the overall interpretation of the results (see text). The lineages of markers tested were: monocyte/macrophage markers, CD68 and cathepsin B; adipocyte marker, adipsin; osteoblast markers, osteoblast-specific cadherin-11, chondroitin sulfate proteoglycan 2, collagen type I alpha 1 and decorin; fibroblast marker, fibronectin; muscle markers, caldesmon and transgelin. Marker signals were normalized to the amount of RNA loaded, which was based on densitometry of the GAPDH signals on the corresponding blot (Bio-Rad Model GS-700 Imaging Densitometer). Attenuation or enhancement of the marker signals in the purified stromal MPCs (i.e., lanes 3 and 4) relative to unfractionated stromal cells (i.e., lanes 1 and 2, respectively) is shown as fold Δ (decrease/increase) underneath the lanes 3 and 4; ND, means not determined.

The purity of the nonhematopoietic cells was demonstrated by a near complete absence of two macrophage markers, CD68 and cathepsin B (as shown by Northern blotting data, FIGS. 6A and 6B). As a positive control, bone marrow mononuclear cells rich in myelomonocytic cells abundantly expressed CD68 (lanes 5 & 6, FIG. 6A). The Northern blot results are consistent with a purity estimate of 95% (vs. 60% in unfractionated samples) based on morphology and immunocytochemical staining for CD68.

Compared to unfractionated cells, the purified nonhematopoietic cells expressed significantly higher levels of markers representing fat cells (adipsin, FIG. 6D); osteoblasts (osteoblast-specific cadherin-11, chondroitin sulfate, collagen type 1 and decorin, FIGS. 6E-6H); fibroblasts (fibronectin, FIG. 6J); and smooth muscle cells (caldesmon and transgelin, FIGS. 6K-6L).

No trace of osteoblast, fibroblast, or smooth muscle cell markers were detected in the bone marrow mononuclear cells, suggesting a less than detectable level of stromal cells or their precursors in bone marrow mononuclear cells. However, the fat cell marker, adipsin, was detected in all samples including the bone marrow mononuclear cells.

Taken together, the morphologic, cytochemical and immunocytochemical results (FIGS. 4A-4H and Table 1), and the Northern blotting data (FIGS. 6A-6M) indicate that the nonhematopoietic stromal cells of the Dexter cultures co-express markers specific for at least four different mesenchymal cell lineages.

This finding is especially intriguing because pluri-differentiation is often a feature of neoplastic cells (Brambilia and Brambilia, Rev. Mal. Respir., 1986, 3:235; Pfeifer et al. Cancer Res., 1991, 51:3793-3801; Tolmay et al. Virchow's Arch, 1997, 430:209-212). However, a cytogenetic analysis of the Percoll-gradient purified MPCs showed a normal GTW banding pattern.

RT-PCR Analysis for Expression of Representative Hematopoietic Growth Factors and Extracellular Matrix Receptors by MPCs: RT-PCR was conducted in a total reaction volume of 100 μl using 2 μg each of total RNA; corresponding primers; and a master mix of the PCR reagents. The RT conditions included sequential incubations at 42° C. for 15 minutes, 99° C. for five minutes, and 5° C. for five minutes. The PCR conditions included: initial melting at 94° C. for four minutes; and cyclical melting at 94° C. for 45 seconds, annealing at 55° C. for 45 seconds and extension at 72° C. for 45 seconds with 34 cycles. PCR was terminated after final extension at 72° C. for ten minutes. Reaction products (G-CSF, SCF, each 25 μl; VCAM-1, ALCAM, each 50 μl; ICAM-1, 75 μl) were concentrated as necessary; electrophoresed along with a 100-bp DNA ladder (GIBCO-BRL) in a standard agarose (1%) gel in TAE buffer; and stained with ethidium bromide.

Figure 6:
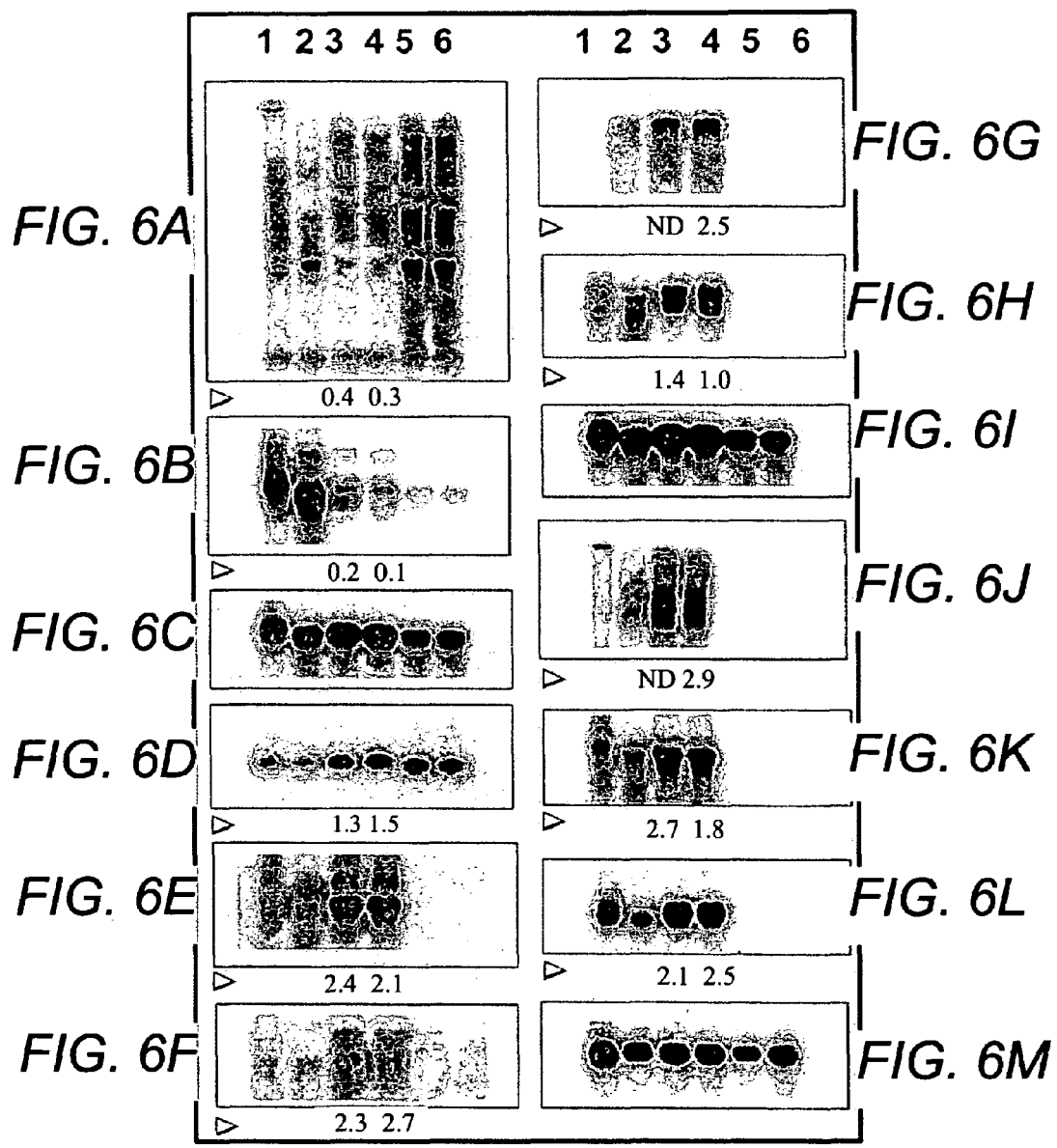
FIGS. 6A-6M are photographs which show Northern blot analysis of bone marrow stromal cell RNAs for expression of genes specific for multiple mesenchymal cell lineages.

PCR products, shown in FIG. 7 lanes labeled 1-2, were generated using aliquots of the same RNA samples from purified stromal MPCs, as used for Northern blotting shown under FIG. 6 lanes 3 and 4 respectively. The gene transcripts amplified were as follows: G-CSF (granulocyte-colony stimulating factor); (Tachibana et al. Br. J Cancer, 1997, 76:163-174); SCF (stem cell factor, i.e., c-Kit ligand); (Saito et al. Biochem, Biophys. Res. Commun., 1994, 13:1762-1769); ICAM-1 (intercellular adhesion molecule-1, CD54) and VCAM-1 (vascular cell adhesion molecule-1, CD106) (primers from R&D); and ALCAM (activated leukocyte cell adhesion molecule, CD166) (Bruder et al. J. Bone Miner. Res., 1998, 13:655-663).

The observed PCR products for G-CSF (600 bp, i.e., the top bright band) and ALCAM (175 bp) were significantly different from the expected sizes (278 bp; 372 bp, respectively). However, sequencing of the gel-purified PCR bands and subsequent BLAST search showed a 99-100% identity with respective members. Attempts to detect c-Kit (i.e., SCF receptor) using primers as described (Saito et al. *Biochem, Biophys. Res. Commun.*, 1994, 13:1762-1769) amplified a PCR product of ~300 bp with no homology to c-Kit (data not shown). The observed product sizes for SCF (~730 bp); ICAM-1 (~750 bp); and VCAM-1 (~500 bp) were as expected.

As illustrated in FIG. 7, RT-PCR analysis showed that purified, multi-differentiated MPCs express both critical hematopoietic growth factor/cytokines, such as G-CSF and SCF as well as matrix receptors/hematopoietic cell adhesion molecules, i.e. ICAM-1, VCAM-1, and ALCAM.

Example 2

Figure 8:
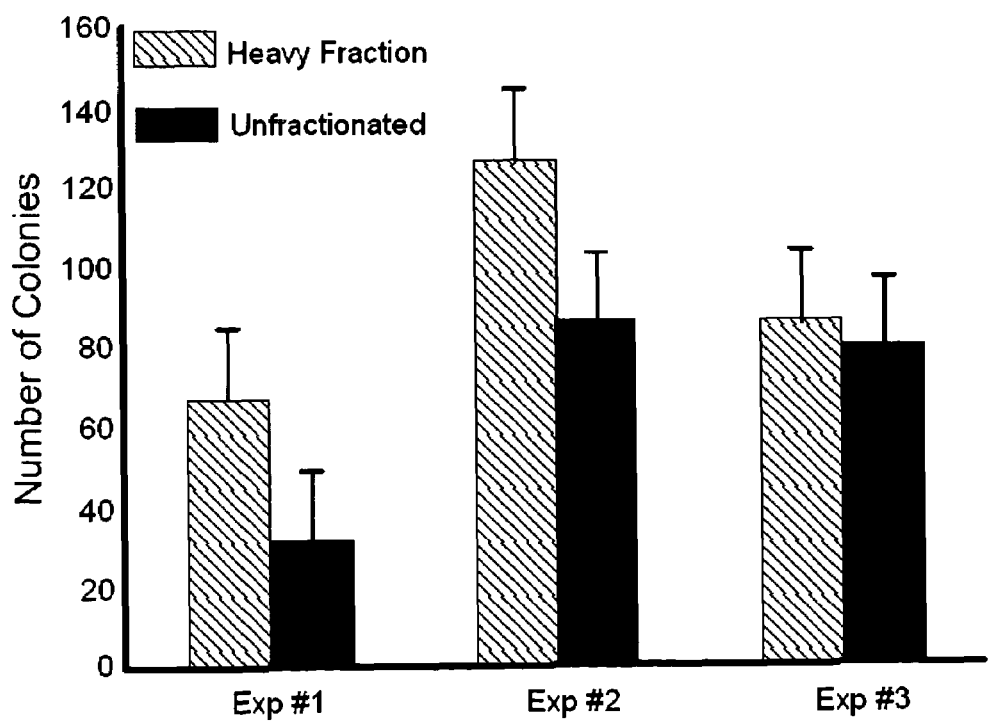
FIG. 8 is a graph illustrating the comparison of the ability to support in vitro hematopoiesis by the purified MPCs (heavy fraction represented by gray) of the present invention vs. unfractionated bone marrow stromal cells (represented by black).

Comparison of the Ability to Support in vitro Hematopoiesis by Purified MPCs vs. Unfractionated Bone Marrow Stromal Cells CD34+ positive cells (hematopoietic progenitor cells) were purified (Dynal kit) and cocultured with irradiated stromal monolayers for five weeks, followed by performance of standard colony assays for hematopoietic progenitors using methylcellulose medium supplemented with colony stimulating factors (using MethoCult medium from Stem Cell Technologies, Inc, Canada). Unfractionated bone marrow stromal cells and purified MPCs were prepared in the same manner as in Example 1. Data in FIG. 8 represents results from three experiments. Purified MPC provides increased preservation of hematopoietic progenitor cells compared to unfractionated stromal cells.

Example 3

Animal Model for Enhanced Engraftment Capacity of MPCs

The Severe Combined Immunodeficiency Disease (SCID) mouse model is an ideal system in which to investigate MPC function. Engraftment of human hematopoietic progenitors in SCID mice requires either coadministration of exogenous human cytokines, or cotransplantation of human bone marrow plugs or bone fragments.

There has been discovered a convenient, new source for human bone marrow stromal cells for enhancing transplantation that does not require cytokines, bone fragment, or marrow. Unlike prior methods, the isolated cells of the present invention support human hematopoiesis in the SCID mouse model as effectively as whole marrow stroma. The transplantation of human marrow mononuclear cells combined with purified MPCs results in dramatically vigorous engraftment of human cells in spleen, bone marrow, liver, pancreas, lungs, stomach, and paravertebral neuronal ganglia of SCID mice. By contrast, mice receiving human bone marrow mononuclear cells alone or MPCs alone expectedly showed no detectable evidence of human hematopoietic cell engraftment. Also notably, the mortality rate was highest in mice that received unfractionated whole marrow stroma whereas purified MPC increased the survival rate which can be due to reduction in GvHD.

Transplantation of Human Cells in SCID Mice: Homozygous CB-17 scid/scid mice, six to eight weeks of age, were used. Lyophilized anti-asialo GM1 rabbit antibody (Wako Chemicals) was suspended in 1 ml sterile ddH$_2$O, followed by pretreatment of mice with an IP injection of 20 ml (600 mg) ASGM1 antibody (to specifically deplete mouse macrophages and NK cells). Alternatively, one could use NOD/SCID mice lacking NK cell function, however, in light of highly promising preliminary results it was elected to continue use of scid/scid mice. The antibody treatment schedule included four-hour pre-engraftment and every seven days thereafter for the duration of the experiment. On the day of transplantation, the mice were irradiated with 200 or 300 cGy gamma-irradiation from a $^{137}$Cs source. Approximately 2.5×10$^6$ MPCs suspended in 0.5 ml McCoy's medium and/or 25×10$^6$ MNCs suspended in 0.2 ml were injected per mouse, intraperitoneally. Hematopoietic cell engraftment was assessed after five weeks by harvesting and analyzing representative hematopoietic and nonhematopoietic organs including blood, spleen, bone marrow (from two femurs and tibia) from euthanized mice.

Figure 9A:
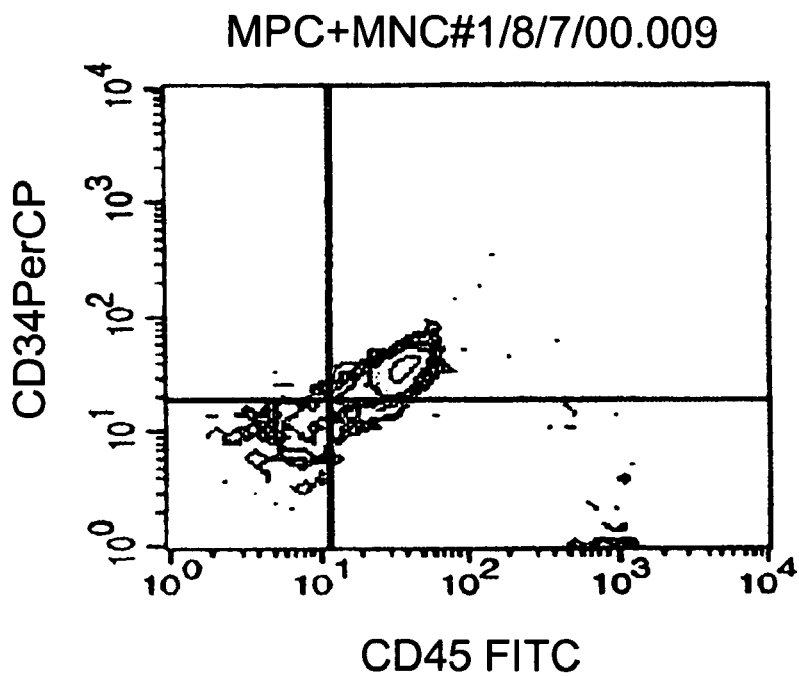
FIGS. 9A-9B are graphs showing flow cytometric evidence of human hematopoietic cell engraftment in a SCID mouse cotransplanted with the MPCs of the present invention.
Figure 9B:
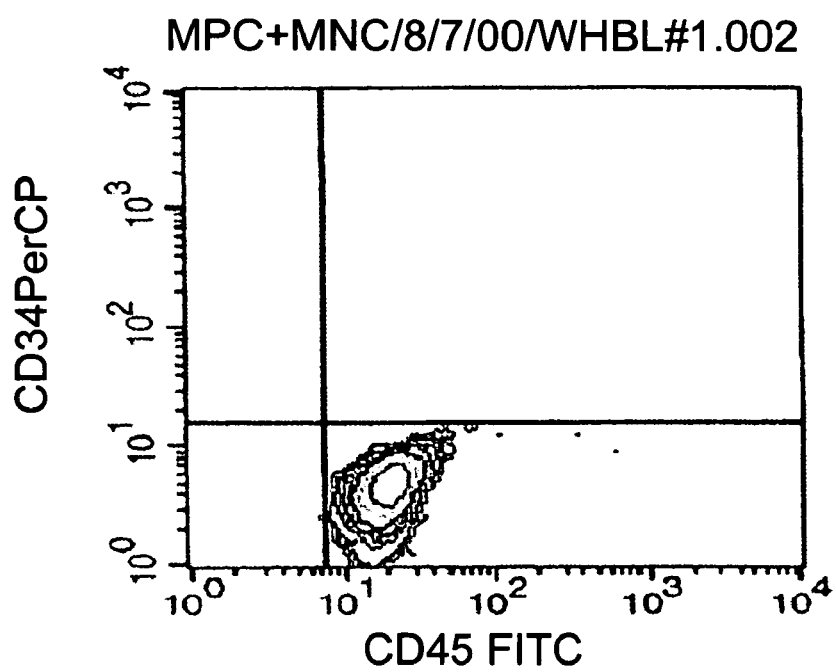

Flow Cytometric Evidence: FIGS. 9A and 9B are flow cytometric evidence of human hemopoietic cells in a SCID mouse cotransplanted with marrow MPC. FIG. 9A shows the presence of CD45+/CD34+ progenitors in the marrow. FIG. 9B shows CD45/CD34− mature hematopoietic cells circulating in the mouse's blood.

Photomicrographs of Cells: FIGS. 10A-10H shows engraftment of human hematopoietic cells in a SCID mouse cotransplanted with the purified marrow MPCs of the present invention. FIG. 10A shows a serial section of a mouse spleen stained with H & E. FIG. 10B shows a serial section of a mouse spleen stained with immunoperoxidase stain for CD45. FIG. 10C shows bone marrow stained for CD45. FIG. 10D shows a serial section of the mouse liver stained with H&E depicting involvement of periportal areas. FIG. 10E shows a serial section of the mouse stomach stained with H&E showing transmural infiltration. FIG. 10F shows a serial section of the mouse lung stained with H&E showing involvement of peribronchial area. FIG. 10G shows a serial section of the mouse pancreas stained with H&E. FIG. 10H shows a serial section of the mouse paravertebral ganglia stained with H&E.

Figure 11A:
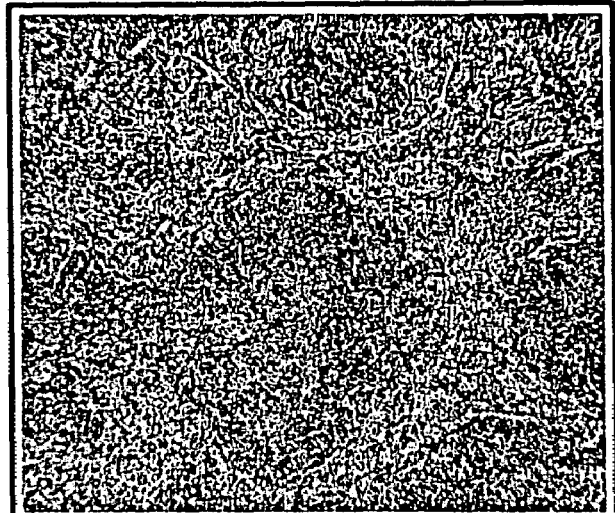
FIG. 11A is a photomicrograph of a serial section of the spleen of a normal BALB/C mouse showing white pulp populated by darkly staining lymphocytes (H&E).
Figure 11B:
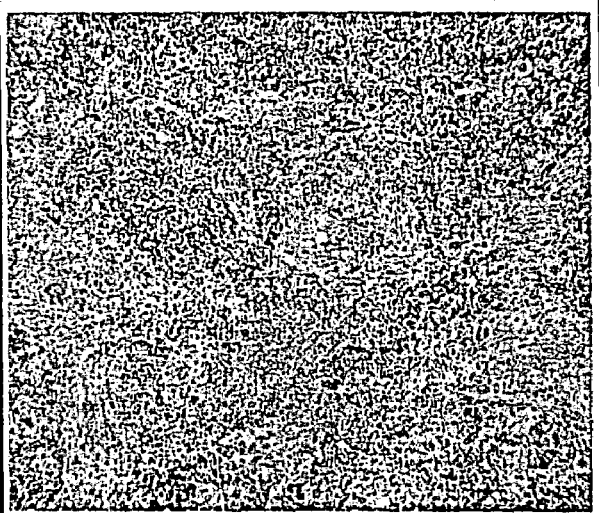
FIG. 11B is a photomicrograph of the spleen of a SCID mouse showing white pulp largely consisting of lightly staining stromal framework (H&E).
Figure 11C:
FIG. 11C is a photomicrograph of the spleen of a SCID mouse cotransplanted with human bone marrow MNC and the purified bone marrow MPCs of the present invention showing homing (engraftment) of human B cells to white pulp.

FIG. 11A is a photomicrograph of a serial section of the spleen of a normal BALB/C mouse showing white pulp populated by darkly staining lymphocytes (H&E). FIG. 11B is a photomicrograph of the spleen of a SCID mouse showing white pulp largely consisting of lightly staining stromal framework (H&E). FIG. 11C is a photomicrograph of the spleen of a SCID mouse cotransplanted with human bone marrow MNC and the purified bone marrow MPCs of the present invention showing homing (engraftment) of human B cells to white pulp.

Figure 12A:
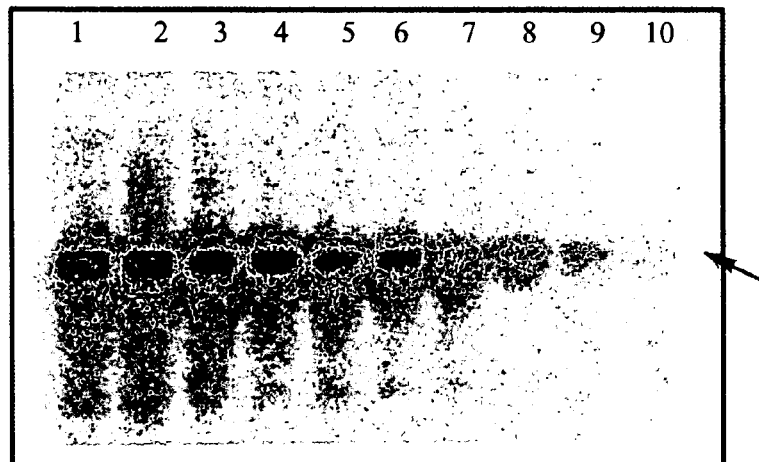
FIGS. 12A-12C are photographs which show Southern blotting data.

Southern Blotting Data: Hybridization of sample DNA using a DNA probe specific for human chromosome 17 alpha satellite DNA (p17H8) shows linear signal intensity with a 2.7 Kb band (arrow; autoradiogram exposed for only 45 minutes) (FIG. 12A). Lanes 1-10 contain human DNA starting 1000 ng to 100 ng admixed with 0 ng 900 ng of mouse DNA, total amount DNA loaded in each lane being 1 ug, allowing construction of a standard curve. The reported limit of detection with this technique is 0.05% human cells, which is more reliable than flow cytometry in detecting very low levels of human cell engraftment.

Figure 12B:
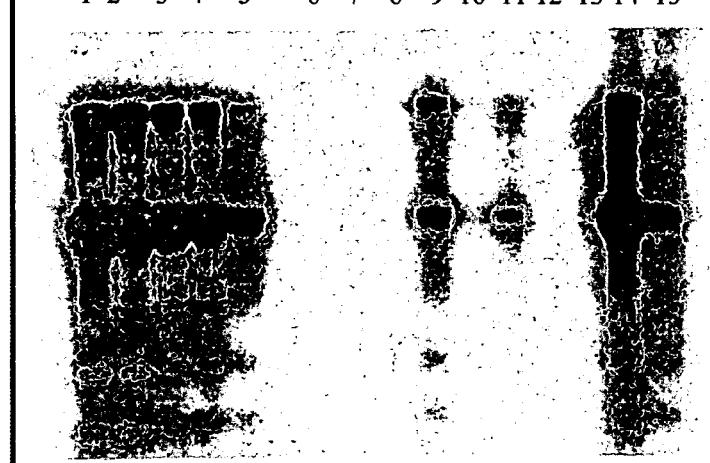

FIG. 12B is a Southern blot of EcoR1 digest of thymic genomic DNA from SCID mice. Lanes 1-5 were loaded with 500 through 100 ng human DNA. Lanes 6, 9-11 were loaded with DNA from mice which received unfractionated bone marrow stroma plus bone marrow mononuclear cells. Lanes 7, 8, 14, 15 were loaded with DNA from mice that received MPCs plus bone marrow mononuclear cells. Lanes 12, 13 were loaded with DNA from mice that received bone marrow mononuclear cells only. There is evidence of human cell engraftment in the mouse thymus in lanes 9 and 11 and lanes 14 and 15 evidenced by the 2.7 Kb band. There was no evidence of engraftment in mice that only received only bone marrow mononuclear cells, lanes 12 and 13.

Figure 12C:
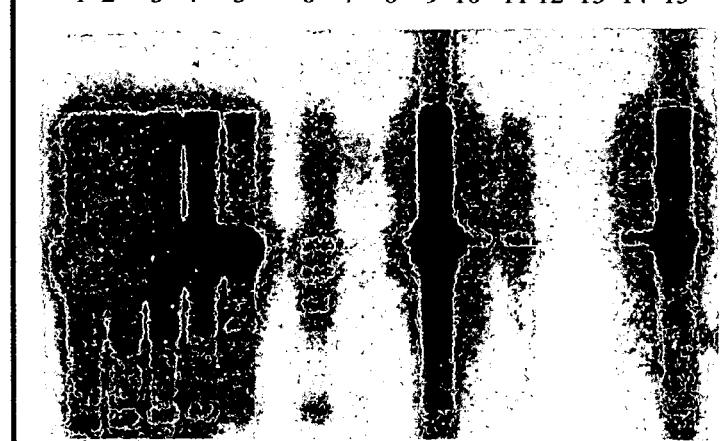

FIG. 12C is EcoR1 digest of Lymph Node genomic DNA from SCID mice. Lanes 1-5 were loaded with 500 through 100 ng human DNA. Lanes 6, 9-11 were loaded with DNA from mice which received unfractionated bone marrow stroma plus bone marrow mononuclear cells. Lanes 7, 8, 14, 15 were loaded with DNA from mice that received MPCs plus bone marrow mononuclear cells. Lanes 12, 13 were loaded with DNA from mice that received bone marrow mononuclear cells only. While there was evidence of engraftment of human cells in the mouse lymph nodes for mice that received unfractioned bone marrow stromal cells and MPCs, there was no evidence of engraftment in mice that only received only bone marrow mononuclear cells, lanes 12 and 13.

Increased Survival and Evidence of MPC Effect on GvHD: FIGS. 13A-1, 13A-2, 13B-1, and 13B-2 show graphs comparing the survival rate and engraftment of human hematopoietic cells in SCID mice cotransplanted with the purified bone marrow MPCs of the present invention versus unpurified marrow stromal cells. Mice in FIGS. 13A-1 and 13A-2 received 300 cGy irradiation dose and mice in FIGS. 13B-1 and 13B-2 received 200 cGY of irradiation. FIGS. 13A-1, 13A-2, 13B-1, and 13B-2 show comparable engraftment of human hematopoietic cells in SCID mice cotransplanted with purified MPCs versus unpurified bone marrow stromal cells and the markedly enhanced survival of mice receiving purified MPCs. Notably, no engraftment was observed in mice receiving bone marrow mononuclear cells alone.

Figure 1:
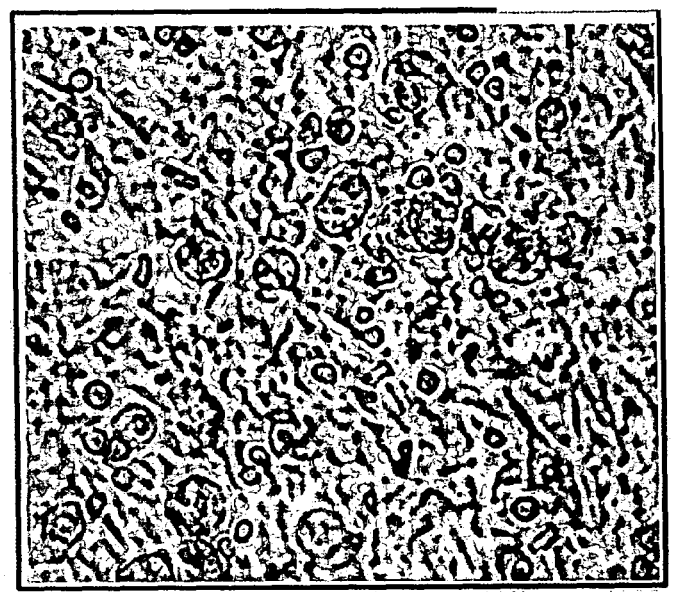
FIG. 1 is a photograph showing the phase contrast photomicrograph view of a Dexter-type stromal cell monolayer reflecting on cellular complexity.
Figures 1, 13A:
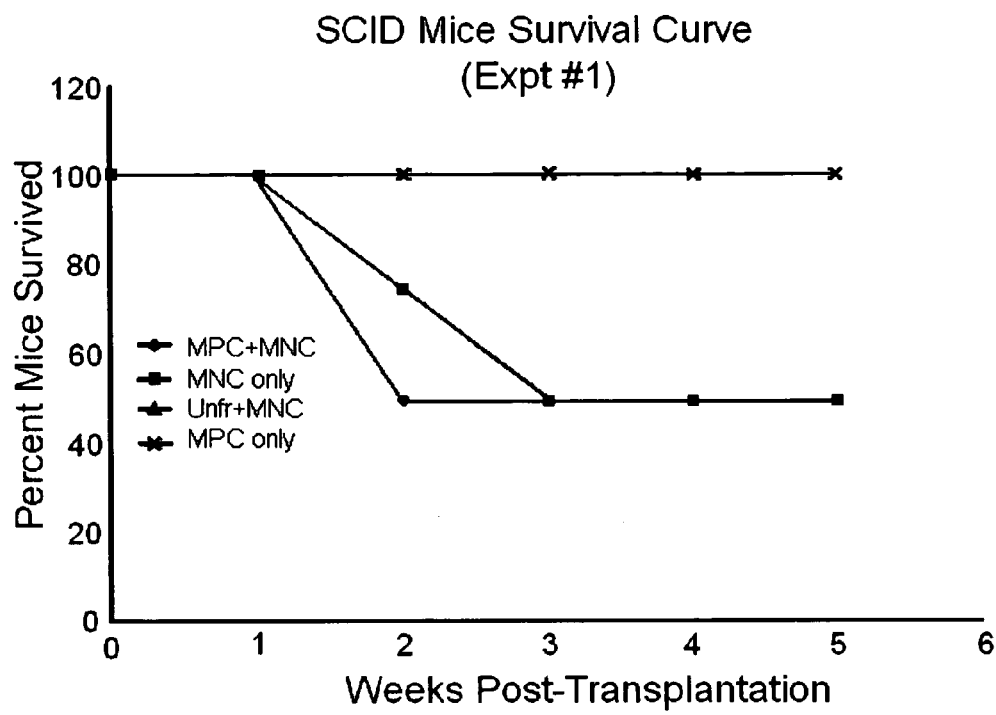
Figures 2, 13A:
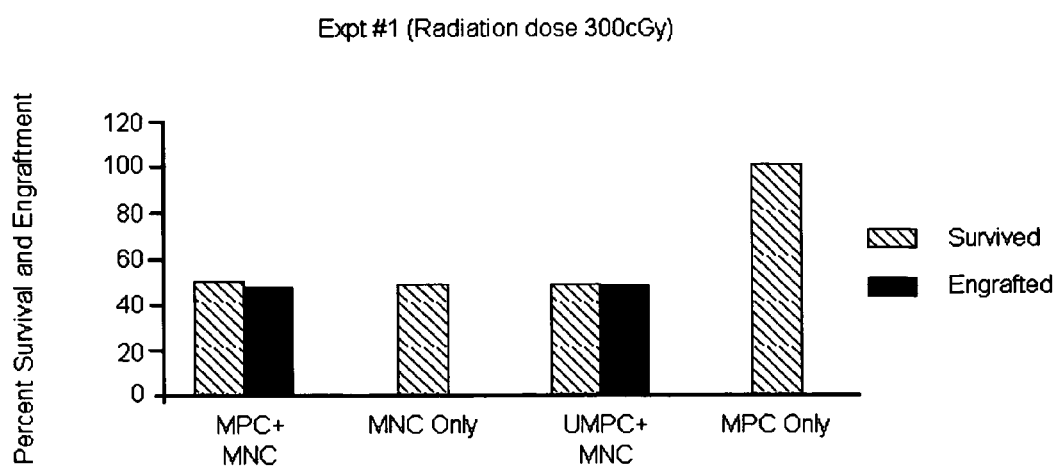
Figures 1, 13B:
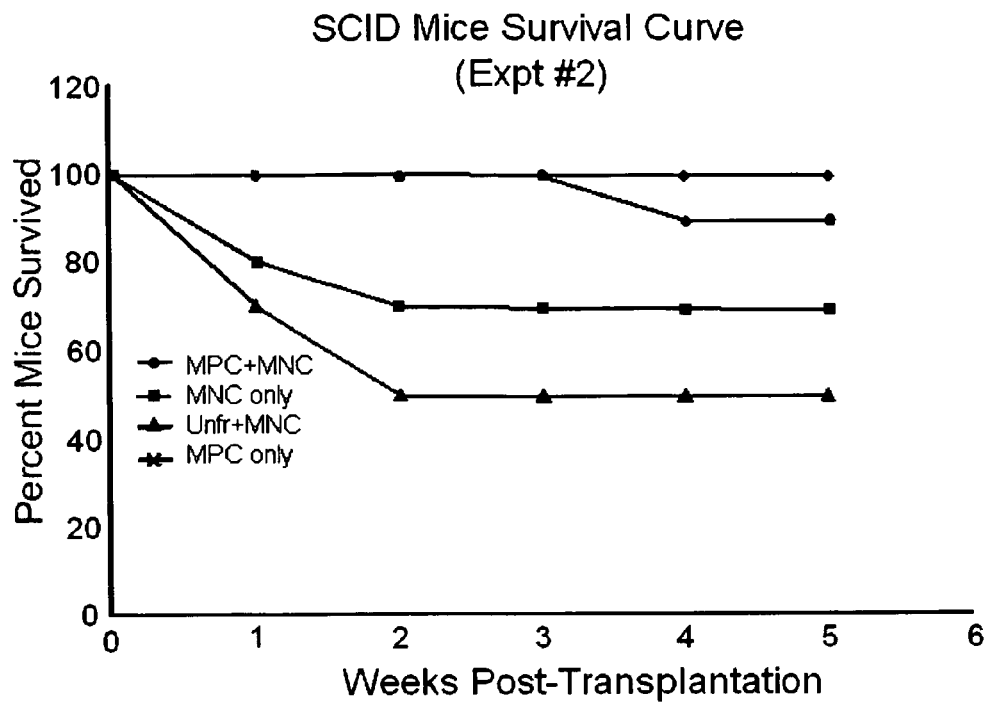
Figures 2, 13B:
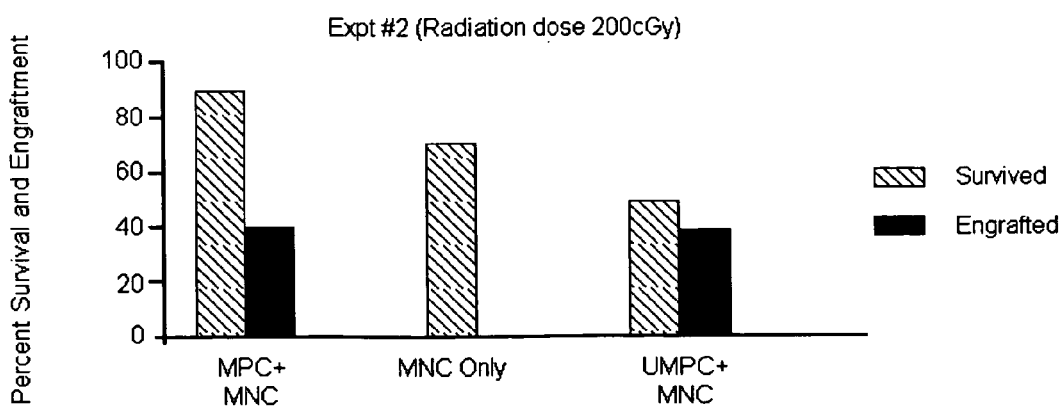

The highest mortality rate, FIGS. 13B-1 and 13B-2, was observed in mice receiving the unpurified stromal cells and the bone marrow mononuclear cells. The increased mortality observed can be related to the presence of highly immunogenic macrophages and consequent GvHD. The mice with the highest survival rate, as shown in FIGS. 13A-1 and 13A-2, were the mice receiving purified MPCs and bone marrow mononuclear cells.

FIGS. 14A-14C demonstrate apoptosis by TUNEL assay in organs of SCID mice that died after transplantation with human bone marrow mononuclear cells and unpurified bone marrow stromal cells. FIG. 14A shows a serial section of the liver of the mouse that survived. FIG. 14B shows a serial section of the liver of the mouse that died. FIG. 14C shows a serial section of the spleen of the mouse that survived. FIG. 14D shows a serial section of the spleen of the mouse that died. Hematoxylin counterstain was applied to sections in FIGS. 14A and 14C. Methylgreen counterstain was applied to sections in FIGS. 14B and 14D.

Notably, there is discrete TUNEL-positive nuclei in the liver of the expired mouse in FIG. 14B and complete absence of staining in the liver of the surviving mouse FIG. 14A. While some ill-defined globules of staining are observed in the spleen of the mouse that survived, the nuclear integrity of most of the cells is well preserved suggesting minimal or no apoptosis (FIG. 14C). By contrast, the dead mouse spleen (FIG. 14D) showed extensive TUNEL positivity precluding accurate interpretation. Control mouse liver and spleen showed results similar to those of the mouse that survived.

The size of the spleens from the mice that survived and the mice that died were compared. The dead mice were observed to have small and atrophic spleens correlating with lymphoid cell depletion and apoptosis.

The above results indicate that purified MPC can support human hematopoiesis in SCID mice as effectively as whole marrow stroma. Equally important is that the purified MPCs increased the survival rate. Evidence suggests that the increased survival can be due to a reduction in GvHD.

Example 4

Administration of Bone Marrow Cells and Mesenchymal Progenitor Cells to Breast Cancer Patients Treated with Chemotherapy A breast cancer patient undergoes a diagnostic posterior iliac crest bone marrow aspiration and biopsy using a local anesthetic. A small portion (2 to 3 ml) of the aliquot (10 to 20 ml) of marrow is submitted for routine histologic testing and determination of the presence of tumor cells using immunoperoxidase testing. The remainder of the cells are Dexter cultured for MPCs as described above in Example 1.

The patient also undergoes placement of a pheresis central venous catheter, and receives subcutaneous injections of G-CSF (filgrastin) 10 µg/kg/day as described in Peters et al. (Peters et al. *Blood*, 1993, 81:1709-1719; Chao et al. *Blood*, 1993, 81:2031-2035; Sheridan et al. *The Lancet*, 1989, 2:891-895; Winter et al. *Blood*, 1993, 82:293a). G-CSF injections begin at least three days before the first pheresis is initiated. G-CSF therapy is withheld if the white blood cell count rises above 40,000 µL and is resumed once the white blood cell count drops to less than 20,000 µL.

If the patient is receiving only G-CSF as the vehicle for "mobilization" of peripheral blood progenitor cells, the patient must not have received chemotherapy within four weeks of the planned pheresis. If the patient has received both conventional chemotherapy and G-CSF treatment for mobilization, the patient must not have received chemotherapy within ten days of the planned pheresis, and the white blood cell count must be at least 800/µL and the platelet count at least 30,000/µL.

Daily pheresis procedures are performed using a Cobe Spectra instrument (Cobe, Lakewood, Colo.), and each cellular collection is cryopreserved using a controlled-rate liquid nitrogen freezer, until at least $15 \times 10^8$ mononuclear cells/kg are collected (Lazarus et al. *Bone Marrow Transplant*, 1991, 7:241-246). Each peripheral blood progenitor cell is processed and cryopreserved according to previously published techniques (Lazarus et al. *J Clin, Oncol.*, 1992, 10:1682-1689; Lazarus et al. *Bone Marrow Transplant*, 1991, 7:241-246).

Eight days before the patient is infused with the autologous peripheral blood progenitor cells, the patient receives chemotherapy over a period of 96 hours (four days), with the following chemotherapy agents: 1) Cyclophosphamide in a total dosage of 6 g/m$^2$ (1.5 g/m 2/day for four days) is given via continuous intravenous infusion at 500 mg/M$^2$ in 1,000 ml normal saline every eight hours; 2) Thiotepa in a total dosage of 500 mg/m$^2$/day for four days) is given via continuous intravenous infusion at 125 mg/m$^2$ in 1,000 ml normal saline every 24 hours; and 3) Carboplatin in a total dosage of 1,800 mg/m$^2$ (200 mg/m$^2$/day for four days) is given via continuous intravenous infusion at 200 mg/m$^2$ in 1,000 ml of 5% dextrose in water every 24 hours.

The patient also receives 500 mg of Mesna in 50 ml normal saline IV over 15 minutes every four hours for six days (144 hours), beginning with the first dose of cyclophosphamide.

At least 72 hours after the completion of the chemotherapy, the MPCs are harvested from the Dexter culture(s). MPCs are collected and purified as described in Example 1. Cells are resuspended at approximately 10$^6$ cells/ml, and injected slowly intravenously over 15 minutes to provide a total dosage of from 10 to about 5×10⁶ cells.

MPCs can also be frozen and thawed to use when needed. For example, unfractionated cells from a Dexter culture are frozen. Upon thawing the cells are plated for about two days. The MPCs are then purified as in Example 1 above. The MPCs are then replated with serum or in a serum free media and can remain stable for up to six days.

The day after the patient receives the MPCs, the frozen autologous peripheral blood progenitor cells are removed from the liquid nitrogen refrigerator, transported to the patient in liquid nitrogen, submersed in a 37° C. to 40° C. sterile water bath, and infused rapidly intravenously without additional filtering or washing steps. GM-CSF in an amount of 250 µg/m² then is given as a daily subcutaneous injection, beginning three hours after completion of the autologous blood progenitor cell infusion. The GM-CSF is given daily until the peripheral blood neutrophil count exceeds 1,000/µL for three consecutive days.

Example 5

Genomic Changes Observed in Leukemia Associated MPCs

The following is one example of how normal hematopoiesis might be compromised in leukemic conditions. The cellular interactions that underlie leukemic bone marrow involve stromal cells, leukemia/lymphoma cells, and normal hematopoietic progenitors (including those of myelopoiesis, erythropoiesis and megakaryocytopoiesis). In addition to displacing normal hematopoietic cells, the leukemia/lymphoma cells can potentially cause direct damage to the hematopoietic supportive stromal cells by inducing unwanted gene expression profiles and adversely affecting the normal hematopoiesis. The cellular interactions can be schematized as:

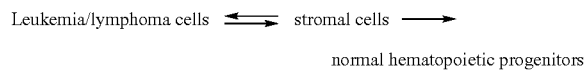

The point of this scheme is that regardless of whether stromal cell lesions are primary or secondary to leukemogenesis, the normal hematopoietic function is invariably compromised in leukemic conditions, though different leukemias affect myelopoiesis, erythropoiesis and megakaryocytopoiesis differentially. Contrary to the prevailing notion (see Marini, F. et al., "Mesenchymal Stem Cells from Patients with Chronic Myelogenous Leukemia Patients can be Transduced with Common Gene Transfer Vectors at High Efficiency, and are Genotypically Normal", 42ⁿᵈ Annual Meeting of the American Society of Hematology, Dec. 1-5, 2000 Poster #665), there has been observed extensive and striking gene expression changes in leukemia-associated bone marrow MPCs by using high-resolution genomics. Therefore, one embodiment of the present invention is to use transplantation of tissue-culture expanded, purified normal MPCs to improve granulopoiesis, erythropoiesis and thrombopoiesis, in for example MDS (most of MDS patients do not die from blast transformation but from complications related to cytopenias, i.e., hematopoietic failure).

The studies targeted acute myeloid leukemia (AML), chronic myeloid leukemia (CML) and multiple myeloma (MM), one case of each. The AML patient was a 57 year-old woman with 52% myeloblasts in the bone marrow with immunophenotype confirmed by flow cytometry and a karyotypic abnormality of 45, XX, -7(6)/46, XX [6]. Together with morphology, the diagnosis was AML arising in a background of myelodysplasia. The CML patient was a 35 year-old man with 2% blasts in the bone marrow and karyotypic abnormalities of Philadelphia chromosome and BCR/ABL gene rearrangement. Together with morphology, the diagnosis was CML in chronic phase. The MM patient was a 61 year-old woman with a IgA myeloma. The serum IgA level was 2.4 g/dl and the marrow plasma cell count was 37%. None of the patients was treated prior to obtaining marrow samples used in this study, to avoid any therapy-induced changes complicating the disease-associated changes.

The leukemic samples consisted of marrow aspirates that remained unused after clinical diagnostic studies were preformed. A bone marrow sample obtained from an adult healthy male who had consented to donate bone marrow for standard marrow transplantation was simultaneously studied. The normal bone marrow sample consisted of residual cells recovered from the filters after complete filtration of the marrow sample. Setting up of Dexter-type stromal cell cultures and isolation of MPC were as described in Example 1. The normal stromal cells were studied without and after stimulation with TNFα because TNFα (and IL-4) are regarded as negative regulators of hematopoiesis. Notably these cytokines, especially TNFα, are elevated in marrow plasma of patients with myelodysplastic syndromes (MDS), the clinical hallmarks of which are anemia, leukopenia and thrombocytopenia (i.e., pancytopenia). TNFα and IL-4 are considered possible mediators of hematopoietic dysregulation typical of MDS.

A Stepwise Genomics Strategy Encompassed: Preparation of total RNA from MPC samples→generation of cDNA→preparation of ds DNA→in vitro transcription into cRNA→fragmentation of cRNA→hybridization of target RNA to a microarray of known genes (Affymetrix genechip containing DNA from ~12,000 known human genes, e.g., U95A oligonucleotide microarray)→analysis of differentially expressed genes using an appropriate software (GENESPRING) to discern the patterns of gene expression or genomic signatures by a given MPC type.

Cluster Analysis Showing Gene Expression Patterns in Bone Marrow MPC Isolated from a Normal Individual and Patients with Different Leukemic Conditions: Genes with correlated expression across bone marrow MPC types: GENESPRING was used for cluster analysis. Prior to application of an agglomerative hierarchical clustering algorithm, microarray signals were normalized across experiments (i.e., from one MPC type to another) making the median value of all of measurements unity, so different experiments are comparable to one another. The signals were also normalized across genes in order to remove the differing intensity signals from multiple experimental readings. Genes that are inactive across all samples were eliminated from analysis. Notably, 7398 genes out of 12,626 genes (present on the Affymetrix genechip used) passed the filter of a normalized signal intensity of at least 0.1 across at least one of the five experiments performed. Cluster analysis was performed with standard correlation (same as Pearson correlation around zero) as the distance metric, a separation ratio of 0.5 and a minimum distance of 0.001 as provided by the software application. A closer relationship between CML- and MM-associated MPCs was observed, which in turn are related to AML-associated MPC, thus transforming global patterns of gene expression into potentially meaningful relationships.

Two-dimensional cluster analysis of tissue vs. gene expression vectors: A gene tree was constructed. Genes cluster near each other on the "gene tree" if they exhibit a strong correlation across MPC experiments and MPC tree branches move near each other if they exhibit a similar gene expression profile. The data indicated that the two-way clustering readjusted the location of a number of genes resulting in accentuation of genomic signatures of each cell type. Investigators can usefully catalog genes composing any unique or signature cluster of interest by creating a gene list and disclosing their identities.

Self-organizing Map (SOM) Clusters (6×5) Show Differential Gene Expression in Bone Marrow MPC Isolated from Different Hematopoietic Conditions: Generation of SOM clusters involved prior normalization and filtering of the data. SOM algorithm was applied as provided by GENESPRING. Visualization of SOM clusters in combination with hierarchical clustering (i.e., MPC tree) revealed correlated meaningful patterns of gene expression. Predicated on the basis of SOM operating principle, the related SOM clusters tend to be located physically close to each other. For example, the juxtaposition of the SOM clusters with the common denominator containing genes that are up-regulated in AML/MDS-associated MPC. Whole or part of any SOM cluster can be selected to make a gene list providing the identities of the genes involved.

Genes Highly Expressed in Normal MPC but Absent or Minimally Expressed in Leukemia-associated MPC: Lists of genes that are down-regulated in leukemia-associated MPC (AMUMDS, CML and MM) were created in comparison to normal MPC. A Venn diagram was made using these three gene lists. GENESPRING allows creation of sublists of genes corresponding to union, intersection and exclusion. Transcriptional profiles of any of these sublists of genes can be visualized across MPC samples of interest. The following is one such sublist of genes containing genes that are highly expressed in normal MPC and down-regulated in leukemia-associated MPCs revealing the identity of the subset of genes of interest: putative, wg66h09.x1 Soares *Homo sapiens* cDNA clone, *Homo sapiens* mRNA for CMP-N-acetylneuraminic acid hydroxylase, *Homo sapiens* cDNA clone DKFZp586G0421 (symptom: hutel), Human mRNA for histone H1x, Putative monocarboxylate transporter *Homo sapiens* gene for LD78 alpha precursor, Interacts with SH3 proteins; similar to c-cb1 proto-oncogene product, wg82b12.x1 Soares *Homo sapiens* cDNA clone, Human atrial natriuretic peptide clearance receptor (ANP C-receptor) mRNA, Human 71 kDa 2'5' oligoadenylate synthetase (p69 2-5A synthetase) mRNA, *Homo sapiens* hMmTRA1 b mRNA, Human GOS2 protein gene, Preproenkephalin, Human guanylate binding protein isoform I (GBP-2) mRNA, Human gene for hepatitis C associated microtubular aggregate protein p44, 17-kDa protein, Human insulin-like growth factor binding protein 5 (IGFBP5) mRNA, GS3686, Human monoamine oxidase B (MAOB) mRNA, Insulin-like growth factor 11 precursor, Human insulin-like growth factor binding protein 5 (IGFBP5) mRNA, Similar to ribosomal protein L21, X-linked mental retardation candidate gene, and *Homo sapiens* mRNA; cDNA DKFZp434A202.

Genes not Expressed in Normal MPC but Highly Expressed in Leukemia-associated MPC: Lists of genes that are up-regulated (instead of down-regulated) in leukemia-associated MPCs (AML/MDS, CML and MM) were created in comparison to normal MPC and a Venn diagram was made. The following is one such sublist of genes containing genes that are inactive in normal MPC but up-regulated in leukemia-associated MPCs revealing the identity of the subset of genes of interest: Beta-tropomyosin, *Homo sapiens* clone 24659 mRNA sequence, Human mRNA for DNA helicase Q1, OSF; contains SH3 domain and ankyrin repeat, ym22b12.r1 Soares infant brain 1 NIB *Homo sapiens* cDNA clone, Human mRNA for pre-mRNA splicing factor SRp20, Human mRNA for golgi alpha-mannosidasell, OSF-2os, *Homo sapiens* gene for Proline synthetase, hk02952 cDNA clone for KIAA0683, wi24g10.x1 *Homo sapiens* cDNA clone, Lysosomal enzyme; deficient in Sanfilippo B syndrome, CTP synthetase (AA 1-591), WD repeat protein; similar to petunia AN11, Human mRNA for 5'-terminal region of UMK, complete cds, *Homo sapiens* chemokine exodus-1 mRNA, complete cds, Human GPI-H mRNA, complete cds, *Homo sapiens* mRNA encoding RAMP1, Transforming growth factor-beta-2 precursor, and *Homo sapiens* mRNA for KIAA0763 protein.

Visualizing Expression of Phenotypically & Functionally Relevant Genes Across Samples of Normal & Disease-associated BM MPC: Although GENESPRING is a highly flexible and user-friendly software application, it lacks the facility to create functionally relevant gene lists containing user-defined key words. This limitation was overcome by devising the following method via MICROSOFT EXCEL. A stepwise protocol to create such a gene list using EXCEL includes: Open the annotated microarray genome file (e.g., Affymetrix U95A) in EXCEL→select the column with gene names→select Data from pull-down menu→Filter→AutoFilter→Custom→enter key words (e.g., cell adhesion or cell cycle)→OK→generates a new EXCEL worksheet with the list of genes containing the key words. Copy and paste the list of genes containing the key words into GENESPRING and save the gene list with a meaningful name. Twenty-two (22) such functionally relevant gene lists (Table 2) were created.

The resulting approach is a simple and powerful way to peer into the expression profiles of focused sets of functionally relevant genes across samples of interest. For example, the human vascular cell adhesion molecule-1 (VCAM-1) gene is completely down-regulated in AML/MDS and the human insulin-like growth factor binding protein (hIGFBP1) gene is up-regulated in AML compared to all other samples. Similarly, *Homo sapiens* gene for LD78 alpha precursor is down-regulated in all of leukemia-associated MPCs. Finally, the lineage markers CD45 and CD68 are essentially absent from the leukemia-associated MPCs attesting to the high degree of purity achieved by the sample preparation technique of the present invention.

RESULTS

The genomic changes observed in leukemia-associated MPCs are striking. As shown in Table 2, the changes (up-regulation and/or down-regulation) involved hundreds of genes. These changes were most dramatic in MPC associated with AML arising in a background of MDS and involved multiple classes of genes (Tables 1-2). Expectedly, the TNFa-induced changes were extensive. Given the high level of purity of MPC preparations, the enormous genomic changes observed are reflective of the underlying pathologic lesions in the MPCs themselves (and not due to the contaminating leukemic cells and/or macrophages). These studies strongly support the hypothesis that stromal cells in a leukemic patient are functionally defective and therefore purified MPCs are of value in restoring the loss of hematopoietic function in leukemic patients.

TABLE 2

Magnitude of global gene expression changes in leukemia-associated and TNFa-stimulated MPCs in comparison to normal MPC

|  | AML/MDS MPC | CML MPC | MM MPC | TNFa MPC |
|---|---|---|---|---|
| # of genes up-regulated | 234 | 112 | 108 | 279 |
| # of genes down-regulated | 379 | 208 | 251 | 164 |

TABLE 3

Functional classes of genes analyzed across normal and leukemia-associated MPCs

| | | |
|---|---|---|
| Annexins (14) | Cell division cycle-related transcripts (36) | IGF system (24) |
| Caspases & apoptosis-related transcripts (33) | Cytokines (19) | Interleukins/receptors (76) |
| Cadherins (50) | Epidermal growth factors and related transcripts (22) | Integrins/disintegrins (70) |
| Calmodulins/calmodulin-dependent kinases (25) | Fibroblast growth factors (21) | Lineage-related markers (19) |
| Cell adhesion molecules (20) | Fibronectins (6) | Laminins (13) |
| Cathepsins (19) | Galectins (6) | Platelet-derived growth factors & receptors (12) |
| Collagens (71) | Growth factors (136) | TNF alpha-related transcripts (29) |
| | | TGF beta-related transcripts (25) |

The gene lists in Table 3 were created as described above and analyzed using GENESPRING. The numerical value in parenthesis refers to the number of transcripts in the corresponding class of genes analyzed.

The invention has been described in an illustrative manner, and it is to be understood that the terminology which has been used is intended to be in the nature of words of description rather than of limitation.

The preceding descriptions of the invention are merely illustrative and should not be considered as limiting the scope of the invention in any way. From the foregoing description, one of ordinary skill in the art can easily ascertain the essential characteristics of the instant invention, and without departing from the spirit and scope thereof, can make various changes and/or modifications of the inventions to adapt it to various usages and conditions. As such, these changes and/or modifications are properly, equitably, and intended to be, within the full range of equivalence of the following claims.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A method for purifying pluri-differentiated mesenchymal progenitor cells comprising the steps of:
   a) providing a cell culture preparation by the Dexter method;
   b) treating the cells to obtain a cell suspension;
   c) removing macrophages;
   d) fractionating the cells; and
   e) collecting the fraction of pluri-differentiated mesenchymal progenitor cells.

2. The method of claim 1, wherein said fractionating of step d) is carried out by discontinuous Percoll gradient centrifugation.

3. The method of claim 1, wherein the collected fraction of pluri-differentiated mesenchymal progenitor cells has a purity of at least 95%.

4. The method of claim 1, wherein the pluri-differentiated mesenchymal progenitor cells are human cells.

5. The method of claim 1, wherein the pluri-differentiated mesenchymal progenitor cells each simultaneously expresses, at the protein level, a plurality of genes that are markers for multiple cell lineages, wherein the multiple cell lineages comprise at least four different mesenchymal cell lineages, and wherein each of the markers is specific for a single cell lineage.

6. The method of claim 5, wherein the at least four different mesenchymal cell lineages comprise adipocyte, osteoblast, fibroblast, and muscle cell.

7. The method of claim 5, wherein the markers specific for a single cell lineage are selected from the group consisting of Nile Red, Oil Red O, adipsin, alkaline phosphatase, cadherin-11, chondroitin sulfate, collagen type I, decorin, fibronectin, prolyl-4-hydroxylase, actin, caldesmon, and transgelin.

8. The method of claim 1, wherein the pluri-differentiated mesenchymal progenitor cells are not neoplastic cells.

9. The method of claim 1, wherein the pluri-differentiated mesenchymal progenitor cells are chromosomally normal, as determined by Geimsa-trypsin-Wrights (GTW) banding.

* * * * *

UNITED STATES PATENT AND TRADEMARK OFFICE
CERTIFICATE OF CORRECTION

PATENT NO. : 7,303,769 B2
APPLICATION NO. : 11/055292
DATED : December 4, 2007
INVENTOR(S) : Beerelli Seshi It is certified that error appears in the above-identified patent and that said Letters Patent is hereby corrected as shown below:

Column 1,
Line 11, "PCT/US10/16408" should read --PCT/US01/16408--.

Column 5,
Line 21, "stromacell cultures" should read --stromal cell cultures--.

Column 6,
Line 56, "EcoR1 digest" should read --EcoRI digest--
Line 57, "EcoR1 digest" should read --EcoRI digest--
Line 66, "represents" should read --represent--
Line 67, "represents" should read --represent--.

Column 7,
Line 67, "Forty $1^{st}$ Annual" should read --$41^{st}$--.

Column 20,
Line 4, "95%" should read -- ~ 95%--.

Column 22,
Line 8, "$25x10^6$" should read --$2.5x10^6$--.

Column 23,
Line 1, "that only received only" should read --that received only--
Line 3, "EcoR1" should read --EcoRI--
Line 15, "that only received only" should read --that received only--.

UNITED STATES PATENT AND TRADEMARK OFFICE
CERTIFICATE OF CORRECTION

PATENT NO. : 7,303,769 B2
APPLICATION NO. : 11/055292
DATED : December 4, 2007
INVENTOR(S) : Beerelli Seshi It is certified that error appears in the above-identified patent and that said Letters Patent is hereby corrected as shown below:

<u>Column 24,</u>
Line 44, "Clin," should read --Clin.--.

Signed and Sealed this

Twenty-fourth Day of June, 2008

JON W. DUDAS
*Director of the United States Patent and Trademark Office*